(12) United States Patent
Lépinay et al.

(10) Patent No.: US 10,677,701 B2
(45) Date of Patent: Jun. 9, 2020

(54) JET FUEL THERMAL OXIDATION TEST EQUIPMENT

(71) Applicant: AD Systems S.A.S., Saint André sur Orne (FR)

(72) Inventors: Martial Lépinay, Mouen (FR); Jean Christien, Fleury-sur-Orne (FR); Florentin Lecornu, Clinchamps-sur-Orne (FR)

(73) Assignee: AD SYSTEMS S.A.S., Saint Andre sur Orne (FR)

( * ) Notice: Subject to any disclaimer, the term of this patent is extended or adjusted under 35 U.S.C. 154(b) by 205 days.

(21) Appl. No.: 15/826,272

(22) Filed: Nov. 29, 2017

(65) Prior Publication Data
US 2019/0162640 A1     May 30, 2019

(51) Int. Cl.
*G01N 7/10* (2006.01)
*B01D 53/26* (2006.01)
(Continued)

(52) U.S. Cl.
CPC .............. *G01N 7/10* (2013.01); *B01D 53/26* (2013.01); *B01F 3/04241* (2013.01);
(Continued)

(58) Field of Classification Search
CPC ...................................................... G01N 33/22
See application file for complete search history.

(56) References Cited

U.S. PATENT DOCUMENTS

| | | |
|---|---|---|
| 5,101,658 A | 4/1992 | Wilson, III et al. |
| 5,337,599 A | 8/1994 | Hundere et al. |

(Continued)

FOREIGN PATENT DOCUMENTS

WO   WO-2009041826 A1 *   4/2009   .......... A61M 5/1452

OTHER PUBLICATIONS

Standard Test Method for Thermal Oxidation Stability of Aviation Turbine Fuels, ASTM International, Conshohocken, PA, pp. 1-21, Jul. 2016.

*Primary Examiner* — Robert A Hopkins
(74) *Attorney, Agent, or Firm* — Vorys, Sater, Seymour and Pease LLP

(57) ABSTRACT

Jet fuels' thermal oxidation characteristics are evaluated via the Standard Test Method for Thermal Stability of Aviation Turbine Fuels. This test method mimics the thermal stress conditions encountered by jet fuel in operation and is often carried out by laboratory devices, known as rigs. The rigs include a test section having a sleeve and a heater tube arranged therein. A pair of bus bars secure the test section to the rig and apply a current to the heater tube. The applied current heats the heater tube and subjects the sample jet fuels that are flowing in the volume between the sleeve and heater tube to high temperatures, which may produce thermal oxidation deposits on the heater tube. Heater tubes are difficult to install, however, and a gauge may be used to ensure accurate placement of the heater tube within the sleeve. In addition, the fuel sample must be prepared via an aeration process, and systems are disclosed for automating the aeration process such that the sample is prepared precisely according to the test standard. Moreover, the rig includes a pump system that moves the fuel sample through the test section, and a pump system is provided in a double syringe arrangement that optimizes fuel flow through the test section without fluctuation. Finally, the rigs include cooling systems for cooling the bus bars and maintaining an appropriate thermal profile within the heater tube, and cooling systems may be provided that independently control the temperature of each bus bar.

9 Claims, 18 Drawing Sheets

(51) Int. Cl.
  *B01F 3/20*    (2006.01)
  *B01F 3/04*    (2006.01)
  *B01F 15/00*   (2006.01)
  *F28F 3/00*    (2006.01)
  *F28F 13/06*   (2006.01)
  *F04B 1/02*    (2006.01)
  *G01N 33/28*   (2006.01)
  *B65D 41/04*   (2006.01)
  *F16B 37/14*   (2006.01)
  *F04B 17/03*   (2006.01)
  *F04B 53/10*   (2006.01)
  *F04B 9/02*    (2006.01)

(52) U.S. Cl.
  CPC .......... *B01F 3/2028* (2013.01); *B01F 3/2057* (2013.01); *B01F 15/00136* (2013.01); *B01F 15/00344* (2013.01); *B65D 41/04* (2013.01); *F04B 1/02* (2013.01); *F16B 37/14* (2013.01); *F28F 3/00* (2013.01); *F28F 13/06* (2013.01); *G01N 33/2805* (2013.01); *B01F 2215/0086* (2013.01); *F04B 9/02* (2013.01); *F04B 17/03* (2013.01); *F04B 53/10* (2013.01)

(56) References Cited

U.S. PATENT DOCUMENTS

| | | |
|---|---|---|
| 8,246,244 B2 | 8/2012 | Youngblood et al. |
| 8,262,283 B2 | 9/2012 | Yang et al. |
| 8,277,118 B2 | 10/2012 | Anderson et al. |
| 8,292,498 B2 | 10/2012 | Anderson et al. |
| 8,371,747 B2 | 2/2013 | Anderson et al. |
| 8,444,314 B2 | 5/2013 | Youngblood et al. |
| 2005/0067413 A1 | 3/2005 | Morris |

\* cited by examiner

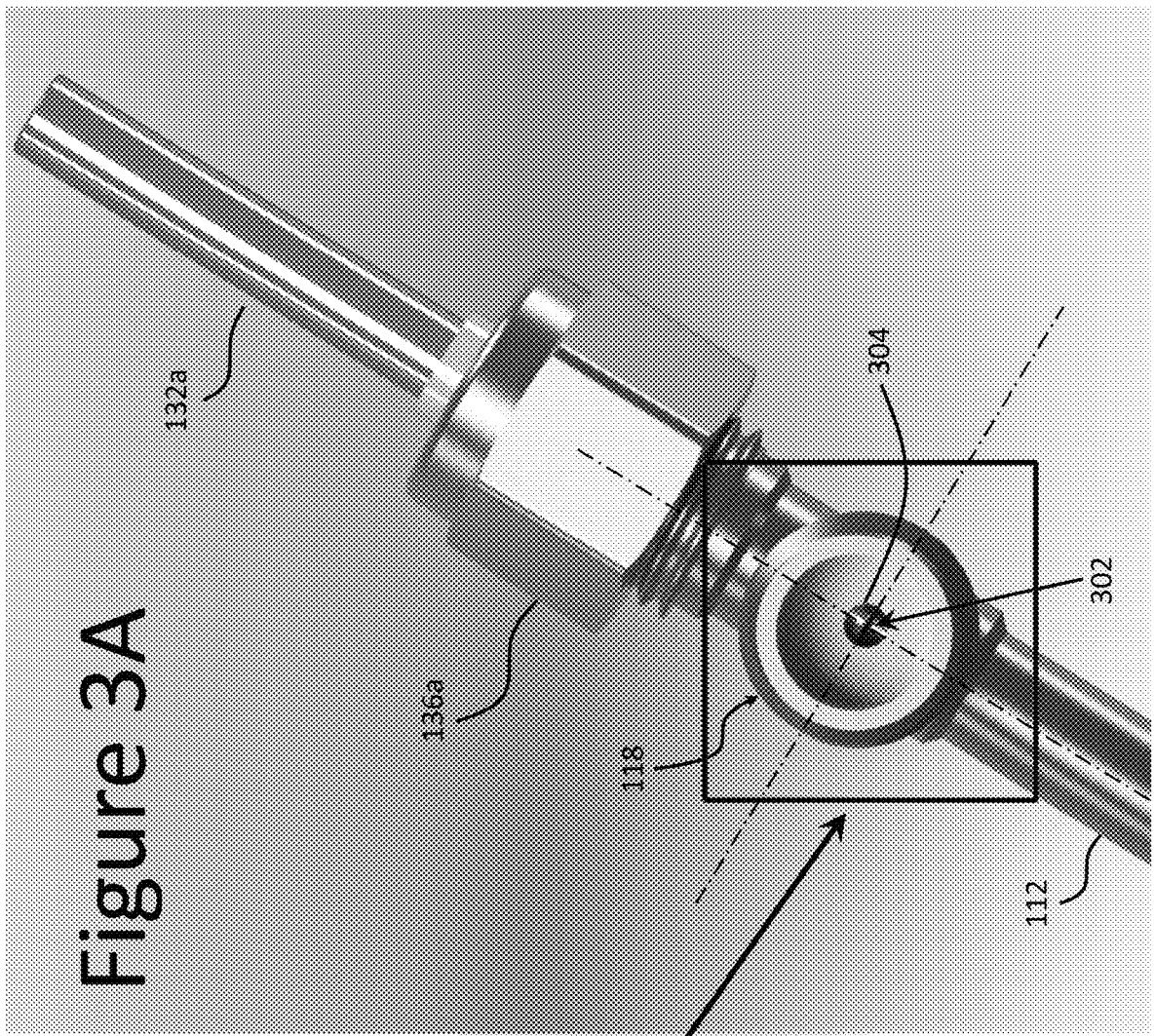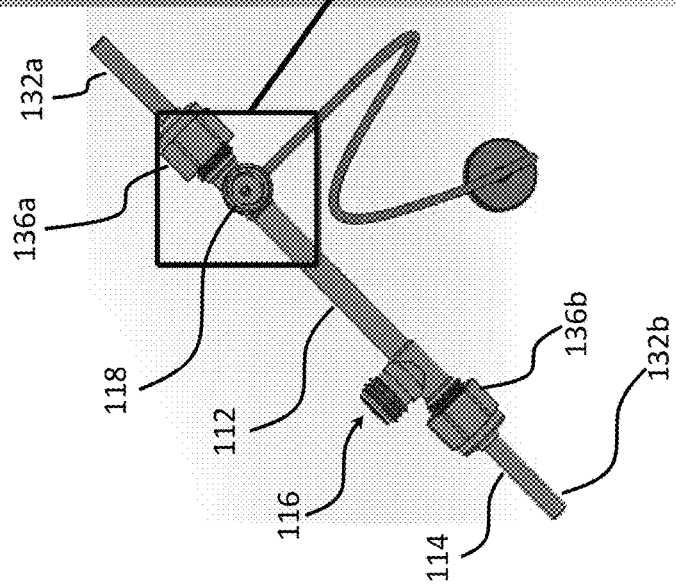

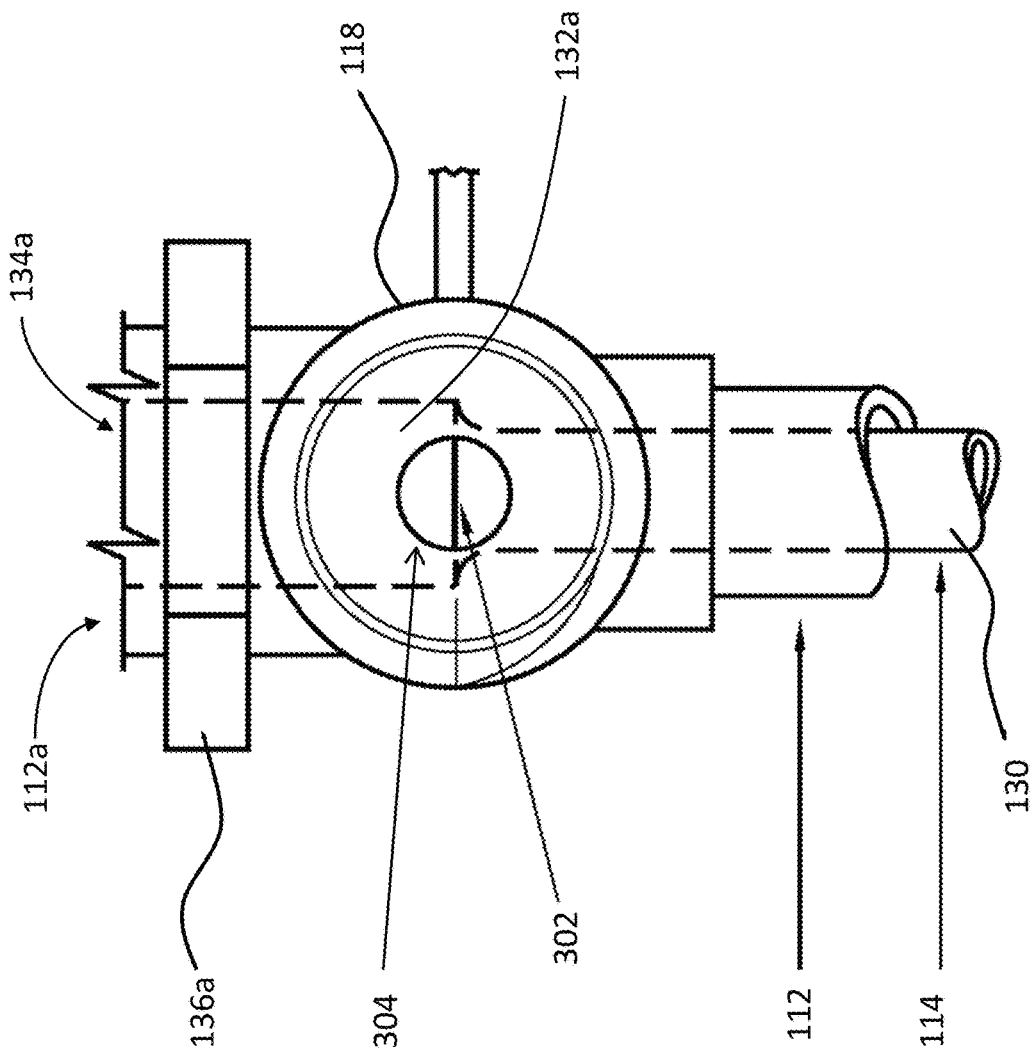

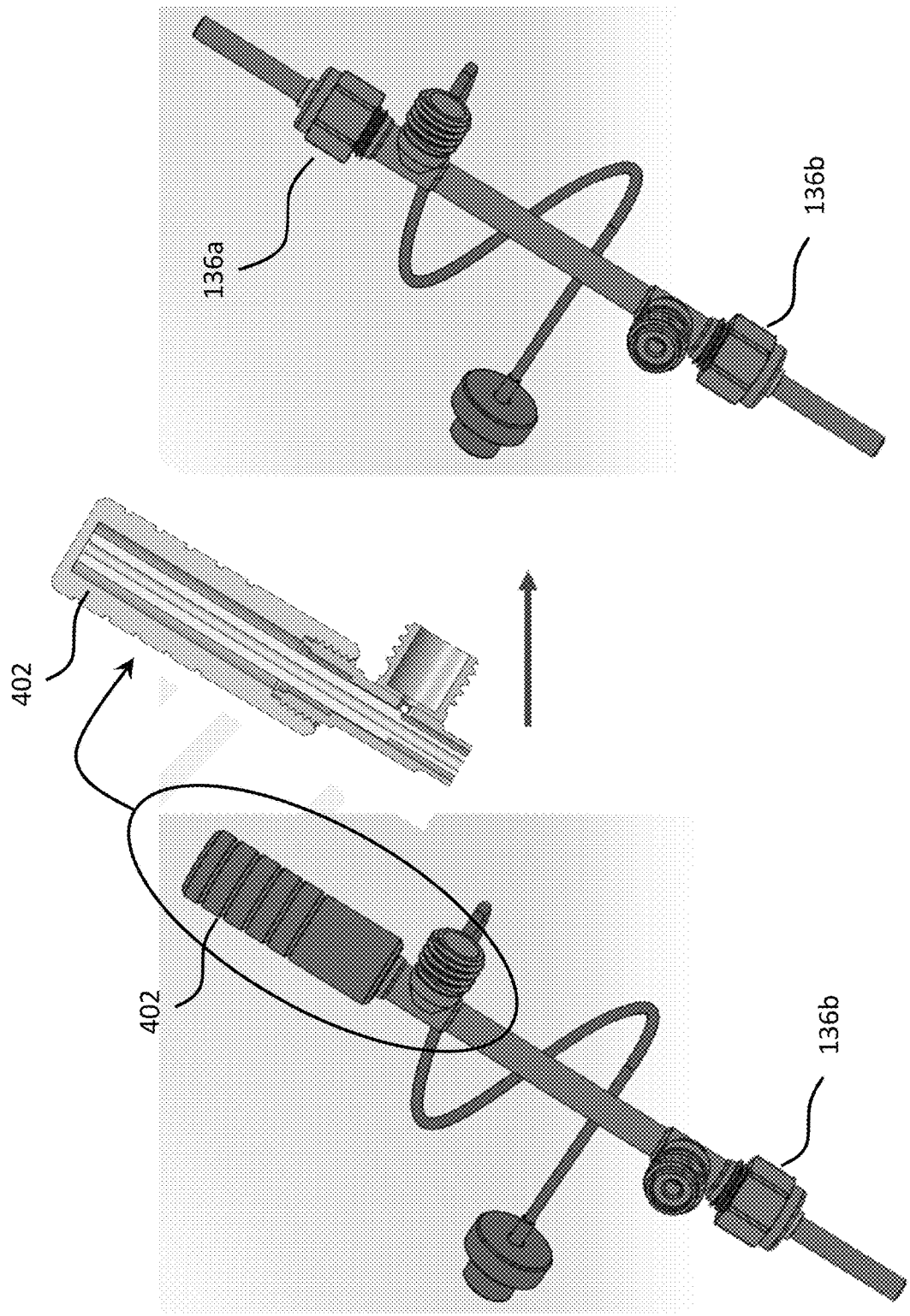

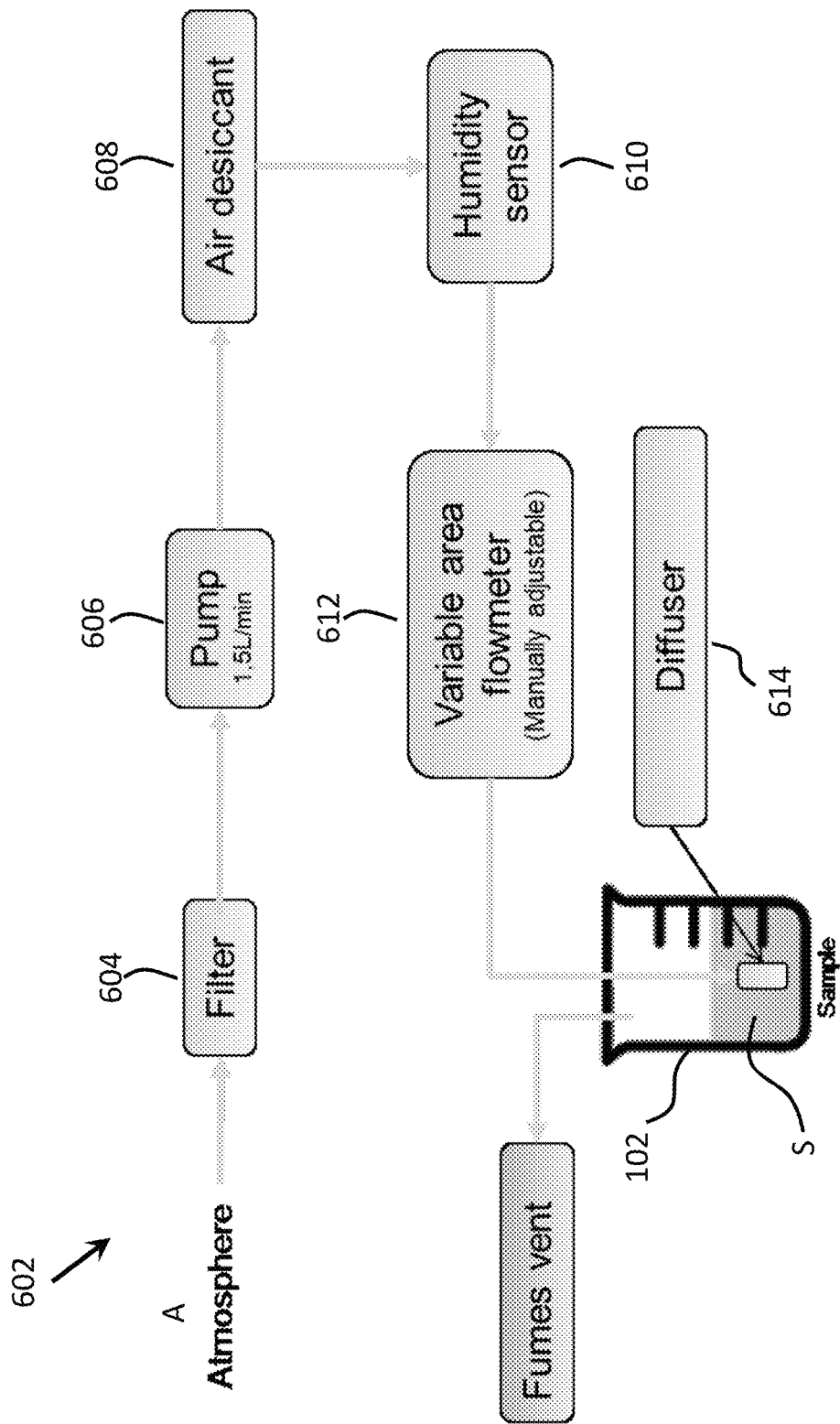

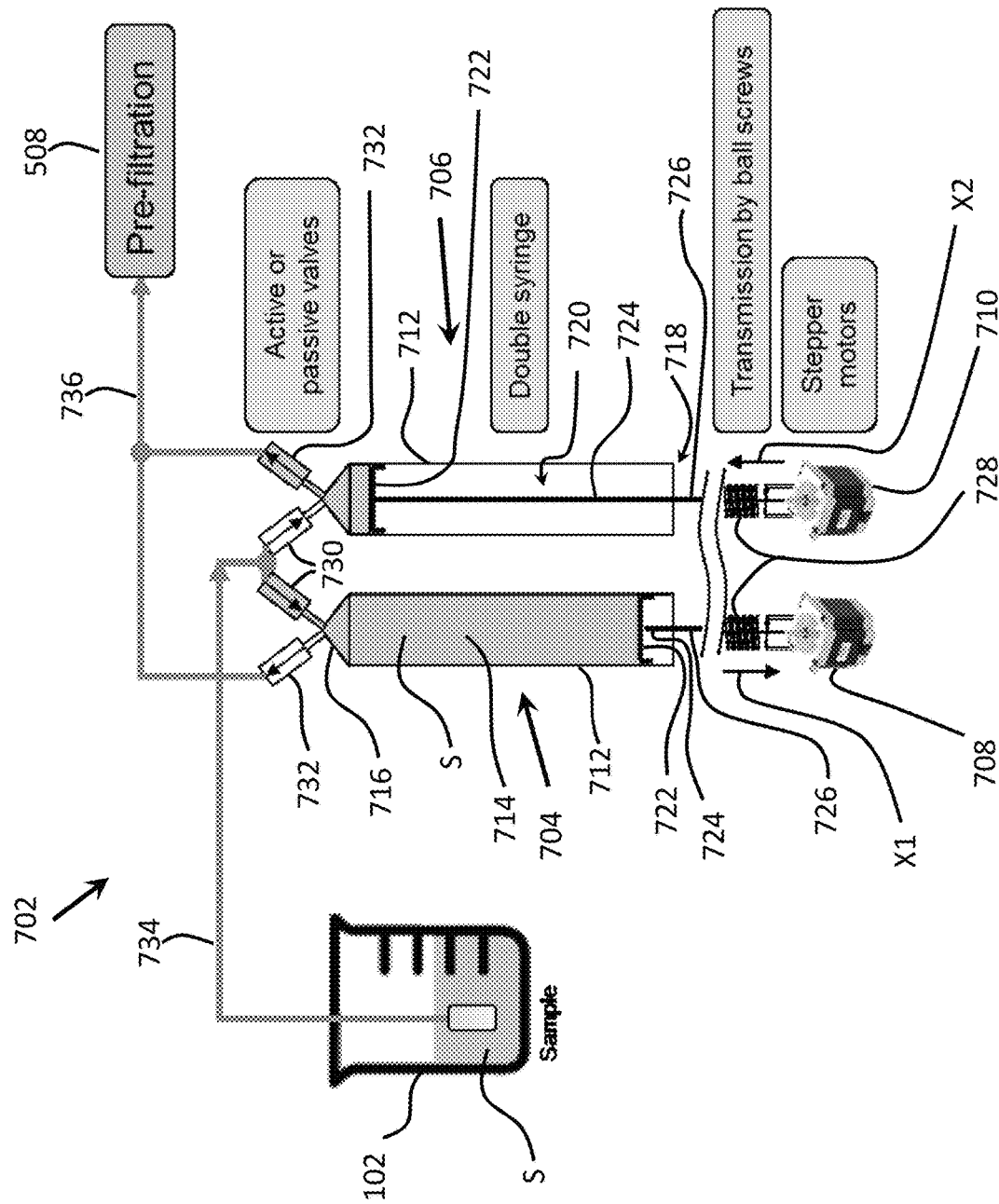

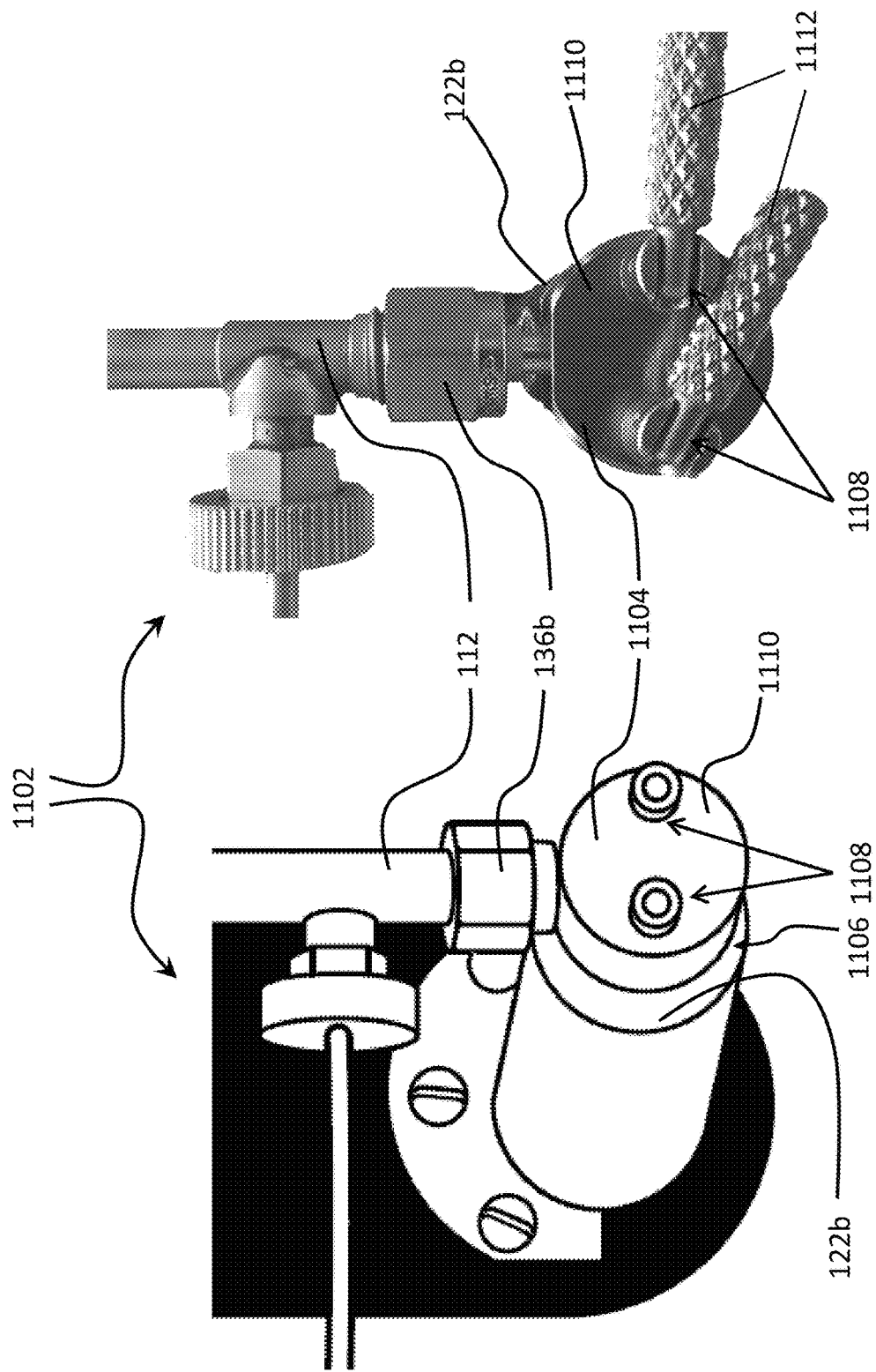

JET FUEL THERMAL OXIDATION TEST EQUIPMENT

FIELD OF INVENTION

The present disclosure is related to jet fuel thermal oxidation testing and, more particularly, to equipment that may be used with jet fuel thermal oxidation testing rigs to improve accuracy, efficiency, and reliability.

BACKGROUND

Modern jet engine systems comprise gas turbine engines that run on jet fuel. Under normal operating conditions, jet fuel is heated by the hot components or regions of the gas turbine engines, which include the fuel nozzles, fuel nozzle support assemblies, and heat exchangers. Modern jet engine systems use the jet fuel's heat sink capability for cooling various aircraft systems, including hydraulic, electronic, and lubrication systems. However, heat management and, ultimately, performance of the jet engine system and airframe is a delicate balance between (i) running fuel systems cooler and incurring performance, cost, and weight penalties by use of air cooling, or (ii) running systems as hot as possible and causing problems associated with unacceptable deposition rates. Accordingly, engineers often design jet engine systems to take maximum advantage of the thermal stability of currently available fuels.

Trends in higher whole engine system performance as well as airframe and engine heat loads, coupled with simultaneous reductions in fuel consumption, are forcing fuel system temperatures to increase even further. Therefore, many modern high performance jet engine systems utilize thermally stressed fuels. At high temperatures, however, less stable species in the thermally stressed jet fuel may undergo oxidation reactions that produce gums, lacquers, particulates, and coke deposits. These resultants may cause a number of problems, including blockage of filters, loss of heat exchanger efficiency, stiction or hysteresis of sliding components in control units, and fouling of injectors and distortion of spray patterns. For example, oxidation of thermally stressed jet fuel may result in deposits or particulate that blocks engine fuel nozzles, thereby causing damage to the engine hot sections due to distorted fuel spray patterns, especially the combustor region. Accordingly, a jet fuel's thermal stability is critical to achieving optimum performance of modern gas turbine engines.

The current standard for evaluating a jet fuel's thermal oxidation is the Standard Test Method for Thermal Stability of Aviation Turbine Fuels, designation D3241, IP323, as published by the American Society for Testing and Materials International ("ASTM International"). This test method mimics the thermal stress conditions encountered by jet fuel in operation and, despite being developed in the early 1970s, remains the best method to evaluate jet fuel thermal stability. More specifically, the D3241 test method sets forth a procedure for rating the tendency of jet fuels to deposit decomposition products within a fuel system. The D3241 test method is performed in two (2) phases. The first phase mimics the fuel conditions present during airplane engine operation, whereas the second phase quantifies the oxidation thermal deposits formed during the first phase.

Various laboratory devices, known as rigs, have been developed since that time to facilitate the D3241 test method. These rigs subject an aluminum heater tube to sample jet fuel under conditions mimicking those encountered during actual engine operation. However, these rigs are difficult to use and require substantial expertise when installing the heater tube within the test section and when preparing the jet fuel sample. Moreover, these known rigs include pump systems that move the fuel sample through the test section, but often have leaks, inconsistent flow rates, and micro-ruptures, and are expensive to operate and maintain. Furthermore, these known rigs have primitive temperature control systems that impact the test results and reproducibility of the same.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 3A is a detailed side view of the sleeve and heater tube assembly utilized in the test section of FIG. 1B and illustrates the fluid outlet when the heater tube is arranged within the sleeve.

FIG. 3B is a cross-sectional side view of the fluid outlet of FIG. 3A.

FIGS. 4A-4B are side views of the sleeve and heater tube assembly of FIG. 3A and illustrate utilization of a gauge to position the heater tube within the sleeve.

FIG. 6A is a diagram that illustrates an example operation of a manual fuel sample aeration procedure.

FIG. 7 is a schematic illustrating an example operation of a pump system having a dual syringe arrangement.

FIG. 11A is a schematic illustrating clamping systems that may be utilized to secure the sleeve and heater tube assembly to the bus bars, for example, at the lower bus bar of FIG. 1B.

DETAILED DESCRIPTION

The embodiments described herein provide positioning gauges for arranging a heater tube within the sleeve of a rig test section. Other embodiments described herein provide air control systems that provide automated aeration of fuel samples with automatic airflow control. Further, embodiments described herein provide pump systems having double syringe arrangements. Moreover, embodiments described herein provide cooling systems that independently control the separate bus bars.

The ASTM International jet fuel thermal oxidation test (D3241, IP 323) standard test method (the "test method") is performed in two (2) phases. The first phase mimics the fuel conditions present during airplane engine operation, whereas the second phase quantifies the oxidation thermal deposits formed during the first part. A technician performs the first phase via an apparatus that simulates conditions present in gas turbine engine fuel systems during operation. The apparatus, referred to herein as a rig, includes a test section that generally comprises a tube-in-shell heat exchanger that holds a test coupon and directs fuel flow over the test coupon. The second phase consists of inspection of the test coupon either via an instrument that automatically measures thermal oxidation deposit thickness or through visual inspection. The following disclosure focuses primarily on the first phase of the test method and the rigs utilized therein to form the thermal oxidation deposit.

Figure 1A:
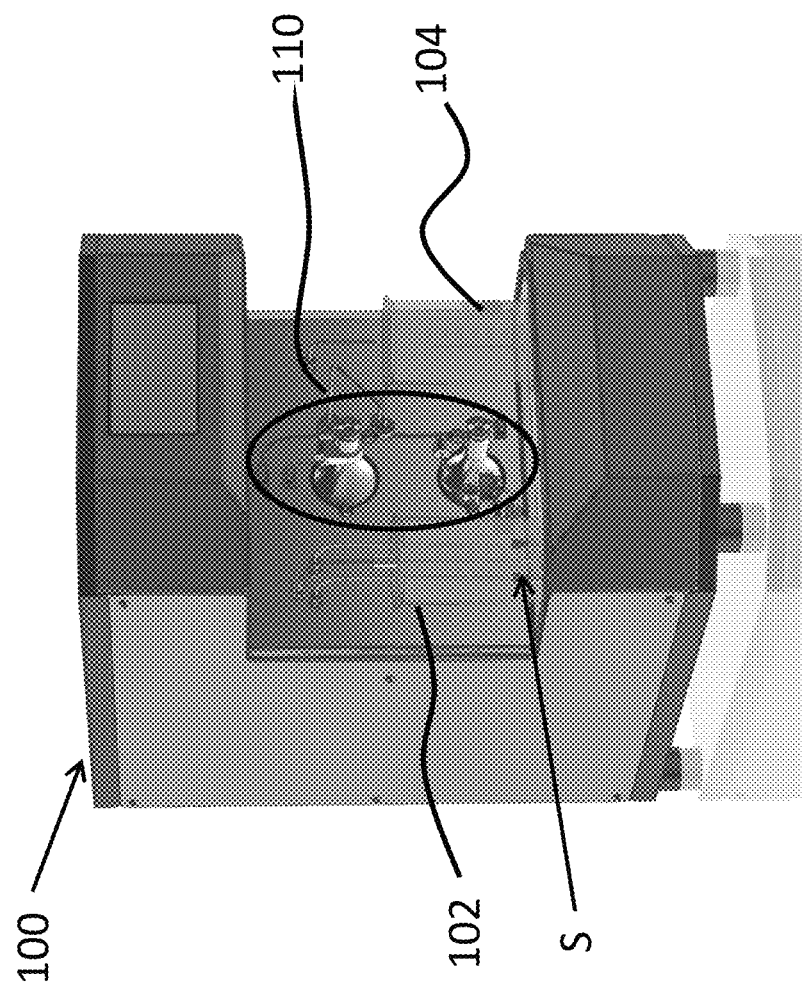
FIG. 1A is a perspective view of an example rig that may incorporate the principles of the present disclosure.

FIG. 1A is a partial perspective view of an exemplary rig 100 that may incorporate the principles of the present disclosure. The depicted rig 100 is just one example testing rig that can suitably incorporate the principles of the present disclosure. Indeed, many alternative designs and configurations of the rig 100 may be employed, without departing from the scope of this disclosure.

In the illustrated embodiment, the rig 100 is configured to automatically perform the test method; however, it may also be configured to automatically perform other petroleum product tests such as ISO 6249. As illustrated, the rig 100 includes a sample container 102, a waste container 104, and a test section 110 that fluidly interconnects the sample container 102 and waste container 104 as hereinafter described. In use, a technician will place a fuel sample S in the sample container 102 and, upon activating the rig 100 to perform the test method, the rig 100 pumps the fuel sample S from the sample container 102, through the test section 110, and into the waste container 102 upon completion of the test method.

Figure 1B:
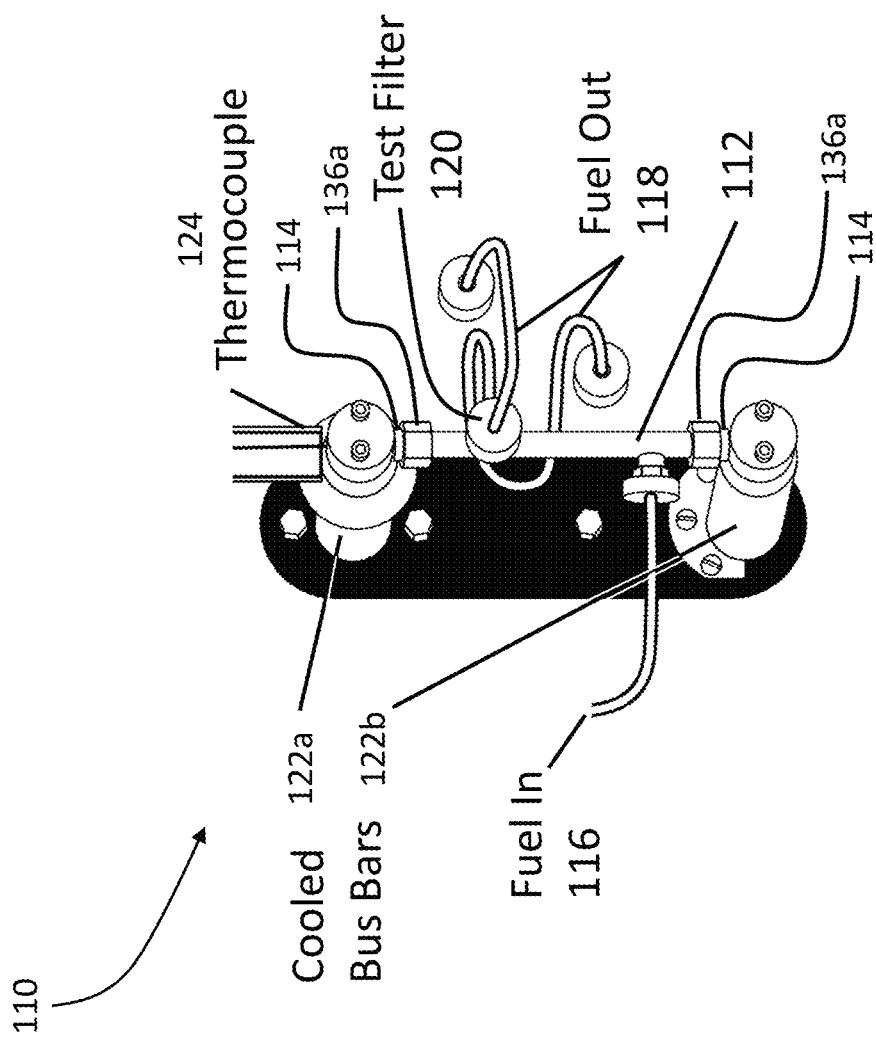
FIG. 1B is a detailed perspective view of the example rig of FIG. 1A, showing an example test section that may incorporate the principles of the present disclosure.

FIG. 1B is a detailed view of the test section 110 of FIG. 1A according to one or more embodiments. As illustrated, the test section 110 may include a sleeve 112 with a heater tube 114 (partially obscured from view in FIG. 1B) hermetically sealed therein. Here, the heater tube 114 is secured within the sleeve 112 via a pair of nut assemblies 136a,136b, however, other assemblies may be utilized to secure heater tube 114 within the sleeve 112 without departing from the present disclosure. The sleeve 112 is hollow and is open at each of its ends 112a,112b (obscured from view in FIG. 1B). The test section 110 also includes a fuel inlet 116 and an outlet 118 arranged on the sleeve 112 between the open ends 112a,112b. The fluid inlet 116 is fluidly connected to the sample container 102 and the fluid outlet 118 is fluidly connected to the waste container 104. In addition, the test section 110 includes a test filter 120 that is arranged proximate to the outlet 118 at a location between the outlet 118 and the waste container 104.

Figure 11B:
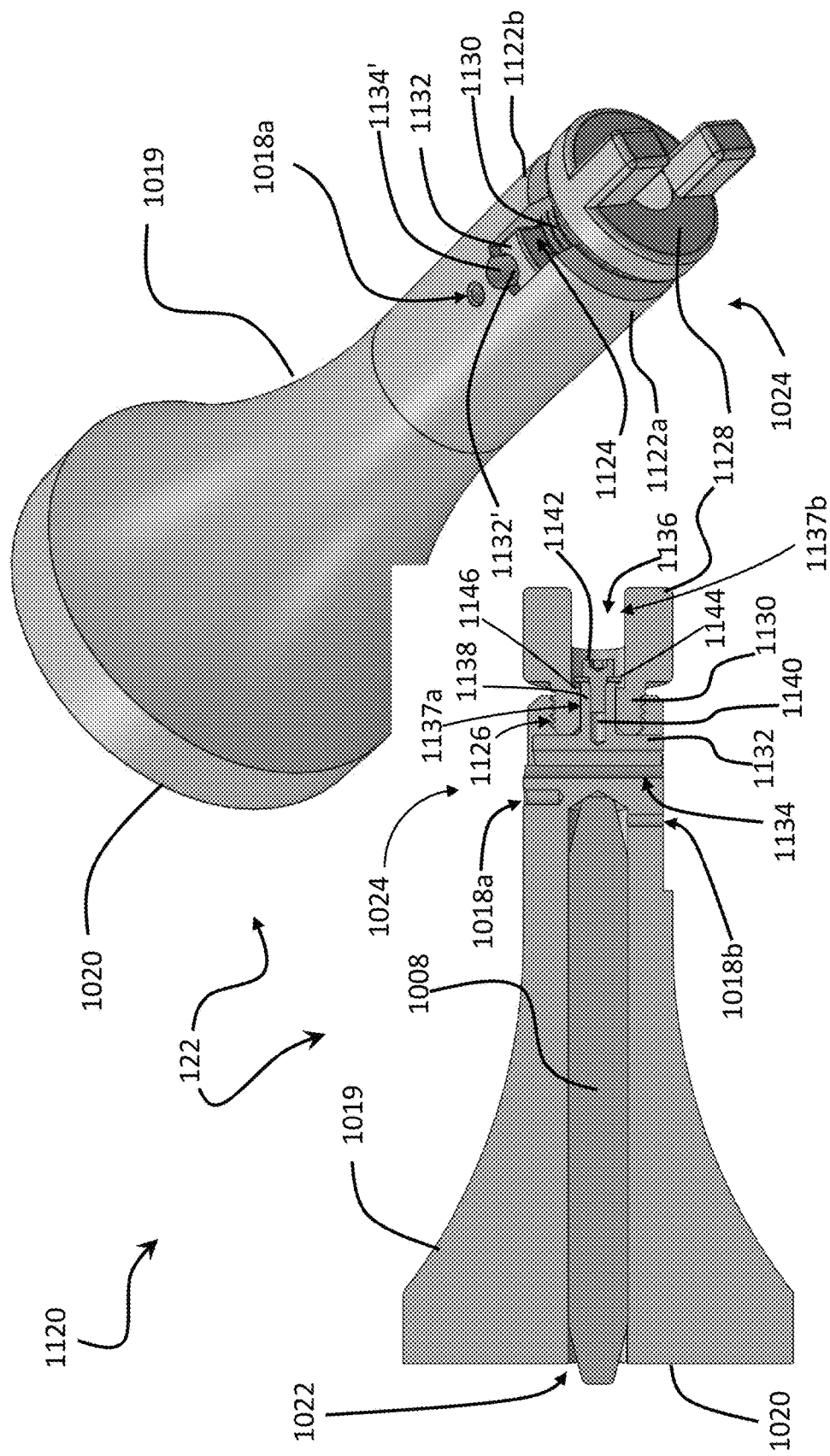
FIG. 11B is a schematic illustrating an alternate clamping system that may be utilized to secure sleeve and heater tube assembly to the bus bars.

FIG. 1B also illustrates the rig 100 comprising a pair of jaws or bus bars 122a,122b that are arranged to secure the test section 110 in a desired orientation via a clamping system which is further described below with reference to FIG. 11A. However, alternate clamping systems may be utilized, for example, as described with reference to FIG. 11B. As described below, the bus bars 122a,122b supply a controlled high amperage, low voltage current to the heater tube 114, thereby making it possible to maintain an accurate temperature during the duration of the test method. Accordingly, the bus bars 122a, 122b are directly or indirectly connected to a transformer or other power supply (not illustrated). In some embodiments, the bus bars 122a,122b are made from brass or other material having a lower thermal conductivity than the heater tube 114 material as hereinafter described. In addition, a thermocouple 124 is arranged to provide temperature measurements of the test section 110 as described below.

Figure 2:
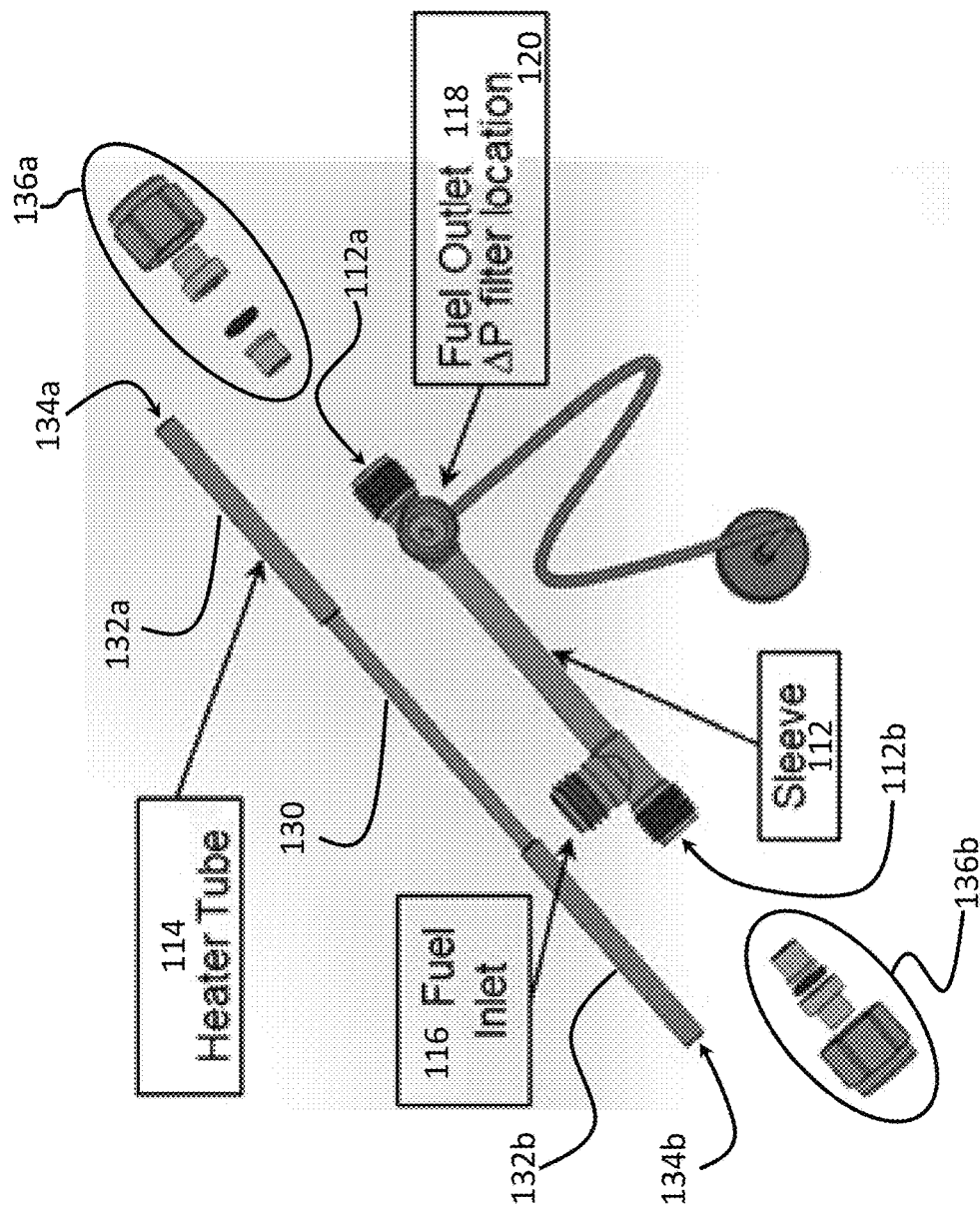
FIG. 2 is a side view of a disassembled test section utilized in the rig of FIG. 1B.

FIG. 2 illustrates a side view of the test section 110 when disassembled and detached from the rig 100. As illustrated, the sleeve 112 is hollow and the fuel inlet 116 and outlet 118 are disposed between the open ends 112a,112b thereof such that the fuel inlet 116, the outlet 118, and the open ends of 112a,112b are in fluid commination with each other. FIG. 2 also illustrates the heater tube 114 when extracted from the sleeve 112, as may occur before and after the test method. As illustrated, the heater tube 114 includes a thin portion 130 interposed between a pair of shoulders 132a,132b disposed at opposing ends 134a,134b of the heater tube 114. In operation, the heater tube 114 is inserted into and through the sleeve 112, and secured thereto via a pair of clamping nut assemblies 136a,136b that permit a technician to remove the heater tube 114 from the sleeve 112, for example, before and after performing the test method. In the illustrated embodiment, the clamping nut assemblies 136a,136b each include gaskets, washers, seals and nuts to secure the shoulder 132a of the heater tube 114 at the open end 112a of the sleeve 112 and to secure the shoulder 132b at the open end 112b. It will be appreciated, however, that the nut assemblies 136a,136b may be differently arranged with the same and/or different components without departing from the present disclosure.

The heater tube 114 also includes a thermocouple (obscured from view) arranged inside an interior volume thereof, and the heater tube 114 is resistively heated by conductance via the pair of bus bars 122a,122b that each clamp a respective one of the pair of shoulders 132a,132b of the heater tube 114. In some embodiments, the heater tube 114 is an aluminum (or other metal) coupon controlled at elevated temperature by the bus bars 122a,122b, over which a fuel sample S is pumped.

As mentioned above, at various points before, during, and after the test method, the technician may need to assemble or disassemble the sleeve 112 and the heater tube 114. For example, the test method may require the technician to precisely assemble the test section 110 (i.e., install the heater tube 114 within the sleeve 112 without any leakage) before beginning the test method and/or to disassemble the test section 110 at the end of the test method. In addition, the test method may call for the technician to clean, rinse, and dry the certain components during the disassembly phase. Accurate analysis and test method results depend on proper assembly, dismantling, cleaning, rinsing, and drying of the test method components. Thus, significant technician expertise is needed to properly perform these phases of the test method, which may consume a significant amount of time and resources.

FIG. 3A-3B illustrates a side view of the heater tube 114 assembled within the sleeve 112 and secured therein via the clamping nut assemblies 136a, 136b. The test method specifies that the heater tube 114 is to be manually positioned within the test section 110 by a technician. More specifically, the test method specifies that the heater tube 114 should be positioned precisely relative to the sleeve 112, and visually adjusted to center a lip 302 of the upper shoulder 132a (of the heater tube 114) within an aperture 304 of the fuel outlet 118 as illustrated in FIG. 3A-3B. This arrangement permits the fuel sample S may flow through the fuel outlet 118 and to other downstream instrumentation, such as the differential pressure measurement instrumentation as hereinafter described.

Once the lip 302 of the upper shoulder 132a has been centered within the fuel outlet 118, the technician will tighten and secure the heater tube 114 within the sleeve 112, for example, via the nut assemblies 136a,136b. Tightening the heater tube 114 within the sleeve 112 will help seal the interior volume through which the fuel sample S flows, however, the resulting clamping forces oftentimes cause unintended repositioning of the heater tube 114 relative to the sleeve 112 such that the lip 302 is no longer properly positioned as mentioned above. Consequently, an extreme fine adjustment is required to pre-position the lip 302 of the heater tube 114 to account or anticipate such displacement during tightening. Accordingly, technicians need significant expertise to properly install the heater tube 114 within the sleeve 112.

Figure 4A:
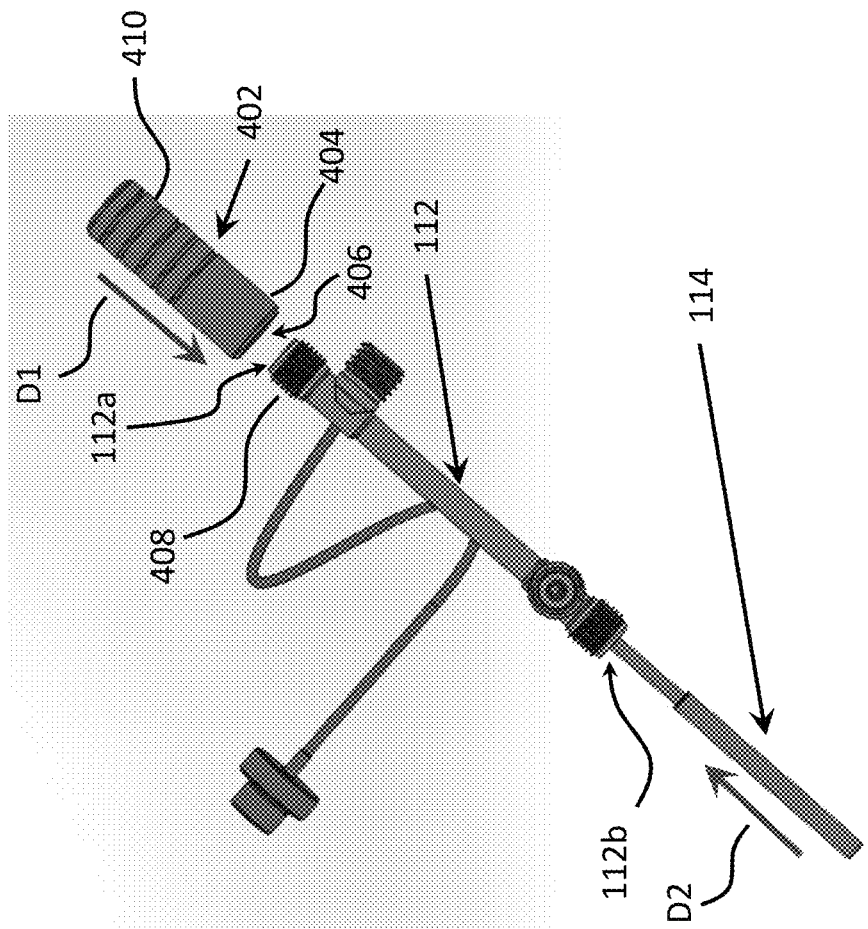

FIGS. 4A-4B illustrate a positioning gauge or gauge 402 that may be utilized to reliably position the heater tube 114 relative to the sleeve 112, according to one or more embodiments. The gauge 402 may be provided as an accessory to assist technicians that would otherwise need to rely on the visual location of the lip 302 within the outlet 118 in order to prepare the test section 110. In the illustrated embodiment, the gauge 402 is open at a first end 404 thereof, and an inner bore 406 of the first end 404 is threaded so that the gauge 402 may be screwed onto an end of the sleeve 112, for example, at a plurality of threads 408 arranged at the open end 112a. In some embodiments, the gauge 402 is open at a second end thereof, and may include a threaded bore at the foregoing second end that includes the same or differently arranged threads, and such arrangements may provide the gauge 402 with the ability to be used with various test sections 110. The body of the gauge 402 includes a central bore that extends a length through the body, and the length that the bore extends may be equal to the body length or shorter. In some embodiments, the bore extends through the body for a length that is shorter than the body and, in such embodiments, a shoulder may be provided along the inner bore surface to act as an abutment that inhibits further axial movement of the shoulder 132a.

Figure 4C:
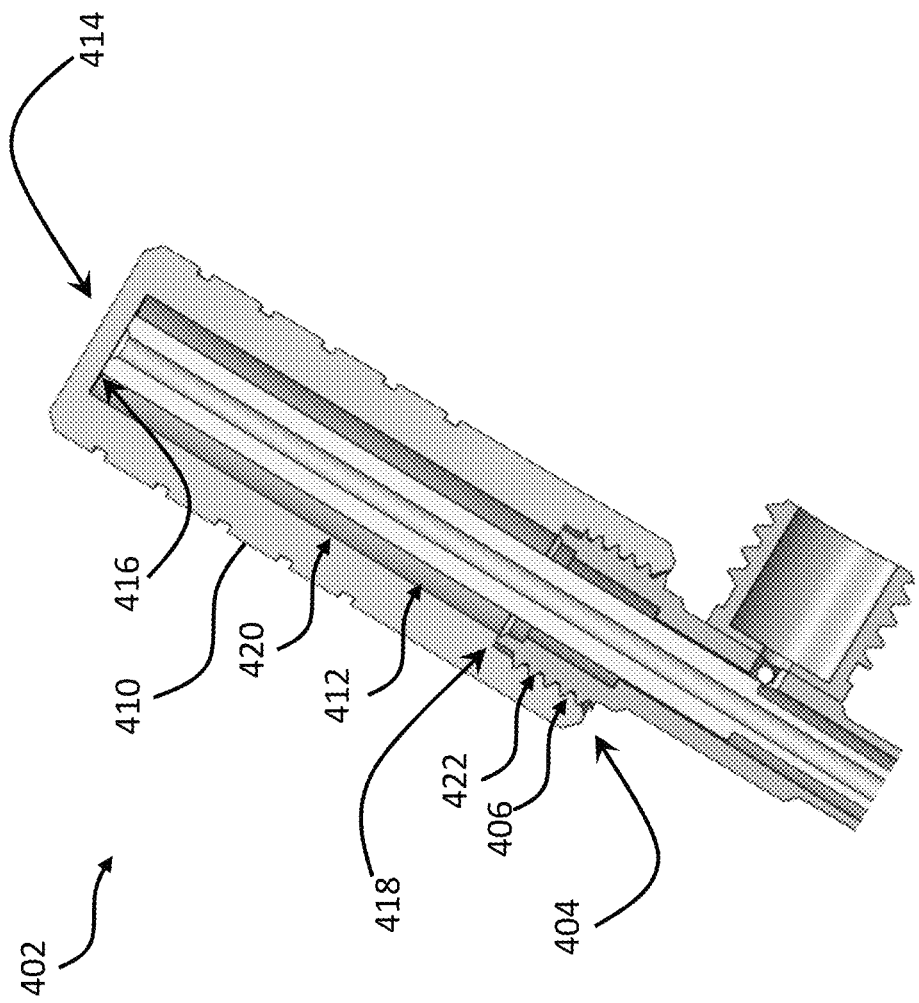
FIG. 4C is a cross-sectional side view of the gauge of FIGS. 4A-4B, which may be used to position the heater tube within the sleeve.

FIG. 4C illustrates an example of the gauge 402, according to one or more embodiments. In the illustrated embodiment, the gauge 402 includes a body 410 that is open at the first end 404 thereof. As illustrated, the body 410 includes a bore 412 extending there-through, from the first end 404 towards a second end 414 that, in the illustrated embodiment, is not open. Accordingly, the bore 412 extends into the body 410 through the first end 404, but stops at a location 416 interposing the first and second ends 404,414. As illustrated, the bore 412 includes the threaded inner bore 406 that extends into the body 410 and terminates at an abutment 418. The bore 412 is also illustrated as including an unthreaded inner bore 420 that extends into the body 410 from the abutment 418 such that the abutment 418 interposes the threaded inner bore 406 and the unthreaded inner bore 420. In the illustrated embodiment, the abutment 418 is arranged as a shoulder that reduces the diameter of the unthreaded inner bore 420 as compared to the threaded inner bore 406; however, in other embodiment, the abutment 418 may be provided as an a protrusion, ring, or other structure that may or may not affect the diameter of the unthreaded inner bore 420. Here, the threaded inner bore 406 is arranged proximate to the first end 404 of the body 410 and includes a plurality of threads 422 arranged to mesh with the threads 408 at the open end 112a of the sleeve 112, whereas the unthreaded inner bore 416 is arranged to interpose the abutment 418 and the second end 414 of the body 410.

In use, a technician positions the first end 404 of the gauge 402 towards the open end 112a of the sleeve 112 in a first direction D1 and screws the threaded inner bore 406 thereof onto the threads 408 of the sleeve 112 at the open end 112a. Then, the technician inserts the heater tube 114 in a second direction D2 into the open end 112b at the bottom of the sleeve 112. After positioning the heater tube 114 within the sleeve 112, the technician clamps the heater tube 114 into position at the bottom end of the sleeve 112, for example, via the nut assembly 136b. Then, the technician removes the gauge 402 and clamps the heater tube 114 into position at the top end of the sleeve 112, for example, via the nut assembly 136a. Thereafter, the technician may tighten the heater tube 114 into position.

Figure 5:
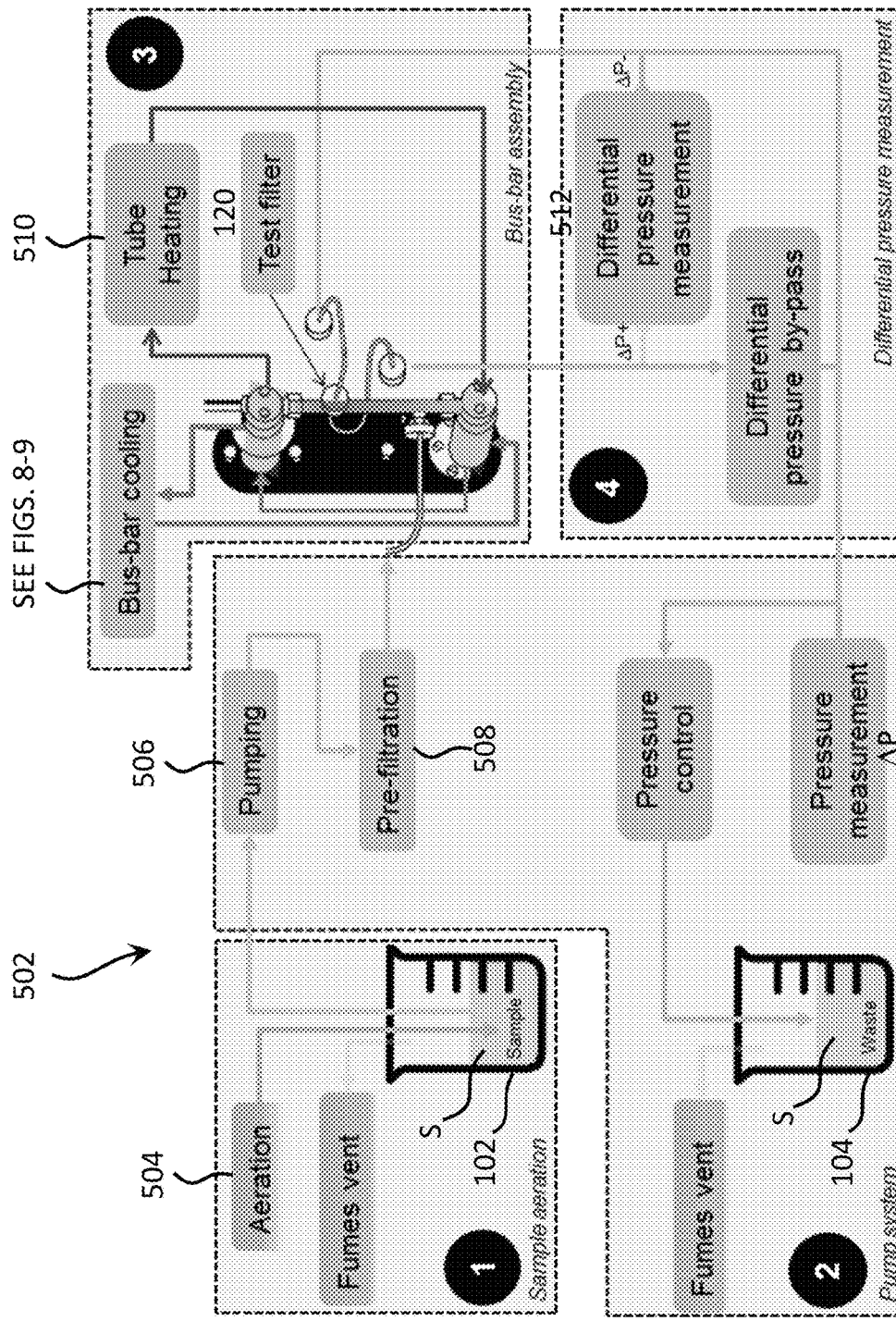
FIG. 5 is a schematic that illustrates various functions of the rig of FIG. 1A that are utilized to aerate the fuel sample.

As previously mentioned, the test method is performed in two (2) parts. First, the test rig 100 is used to create the thermal oxidation deposit. Second, a dedicated instrument is utilized to quantify thermal oxidation deposit formed during the first phase. FIG. 5 illustrates a sequence of functions 502 performed by the rig 100 during the first part of the test method to create the thermal oxidation deposit, according to one or more embodiments. As illustrated, the sequence of functions 502 includes an aeration step or procedure 504, a pre-filtration step or procedure 508, a bus bar cooling step or procedure, a tube heating step or procedure 510, and a differential pressure measurement step or procedure 512. The bus bar cooling will be detailed below.

The fuel sample S is a fixed volume of fuel and stored in the sample container 102. The rig 100 utilizes a pump system 506 to move or pump the fuel sample S at a steady rate from the sample container 102, through the test section 110 and across the heater tube 114, and finally into the waste container 104. The fuel sample S may degrade on the heated heater tube 114 to form thermal oxidation deposits that may appear as a visible film thereon. In addition, degraded materials from the fuel sample S may flow downstream from the heater tube 114 and, for example, be caught in the test filter 120.

Accordingly, the fuel sample S is first prepared by aerating or saturating it with dry air via the aeration procedure 504. After the aeration procedure 504, the rig 100 subjects the fuel sample S to the pre-filtration step 508, for example, by pumping the fuel sample S through a paper membrane. In one embodiment, the paper membrane of the pre-filtration step 508 is a 0.45-μm membrane filter. The pump system 506 then moves fuel sample S at a fixed volumetric flow rate into the test section 110 through the fluid inlet 116 of the sleeve 112. The fuel sample S flows through the test section 110, between an inner wall of the sleeve 112 and an outer wall of the heater tube 114, and exits the sleeve 112 through the outlet 118 thereof. After exiting the sleeve 112, the fuel sample S passes through the test filter 120 and the rig 100 performs the differential pressure measurement step 512.

In the illustrated embodiment, the differential pressure measurement step 512 includes estimating an obstruction rate of the test-filter 120 by conducting a differential pressure measurement between the pressure in the lines upstream of the test filter ($\Delta P+$) and the pressure in the lines downstream of the test filter ($\Delta P-$). The obstruction rate, hereinafter referred to as a differential pressure drop ($\Delta P$), across the test filter 120 is measured by mercury manometer or by electronic transducer. The rig 100 may also include a differential by-pass line having a valve that may be selectively opened or closed to facilitate flow of the fuel sample S through the by-pass line. If, for example, the differential pressure drop ΔP across the test filter 120 begins to rise sharply (and the technician desires to run the full test method), the valve of the bypass line may be opened in order to finish the test method.

As briefly detailed above, the test method requires a technician to prepare the fuel sample S via the aeration procedure 504. More specifically, the test method directs the technician to inject dry air in the fuel sample S that is contained in the sample container 102 at a rate of 1.5 liters ("L") per minute ("min") for 6 minutes prior to performing the test method. Existing instruments, however, utilize manual airflow adjustment that may affect or influence the accuracy and reproducibility of the test method results. FIG. 6A illustrates an exemplary aeration procedure 502 comprising a number of manual aeration sequence 602 that is utilized by existing instruments. As illustrated, the manual aeration sequence 602 (sometimes referred to as the aeration phase) begins with providing air A at atmospheric pressure, and then pumping that air A through a filter 604 at a rate of 1.5 L/min via a pump 606. The pre-filtered air A is then subject to a drying process, for example, via an air desiccant 608 and humidity sensor 610, that collectively dry and measure the amount of moisture present within the air A. The air A is then directed into a variable area flowmeter 612 that is manually adjusted to ensure that the air A is injected into the sample container 102 at the desired rate to ensure adequate aeration. In the illustrated embodiment, the air A is directed from the variable area flowmeter 610 into a diffuser 614 arranged within the sample container 102 and, as prescribed by the test method, the diffuser 614 may be a coarse 12-millimeter ("mm") borosilicate glass dispersion tube. As will be appreciated, aeration of the fuel sample S results in fumes that are vented from the system via a ventilation system. However, the aeration sequence 602 is manual and, depending on the technician's skill and operation of the variable area flowmeter 612, the test method results may or may not be accurate.

Figure 6B:
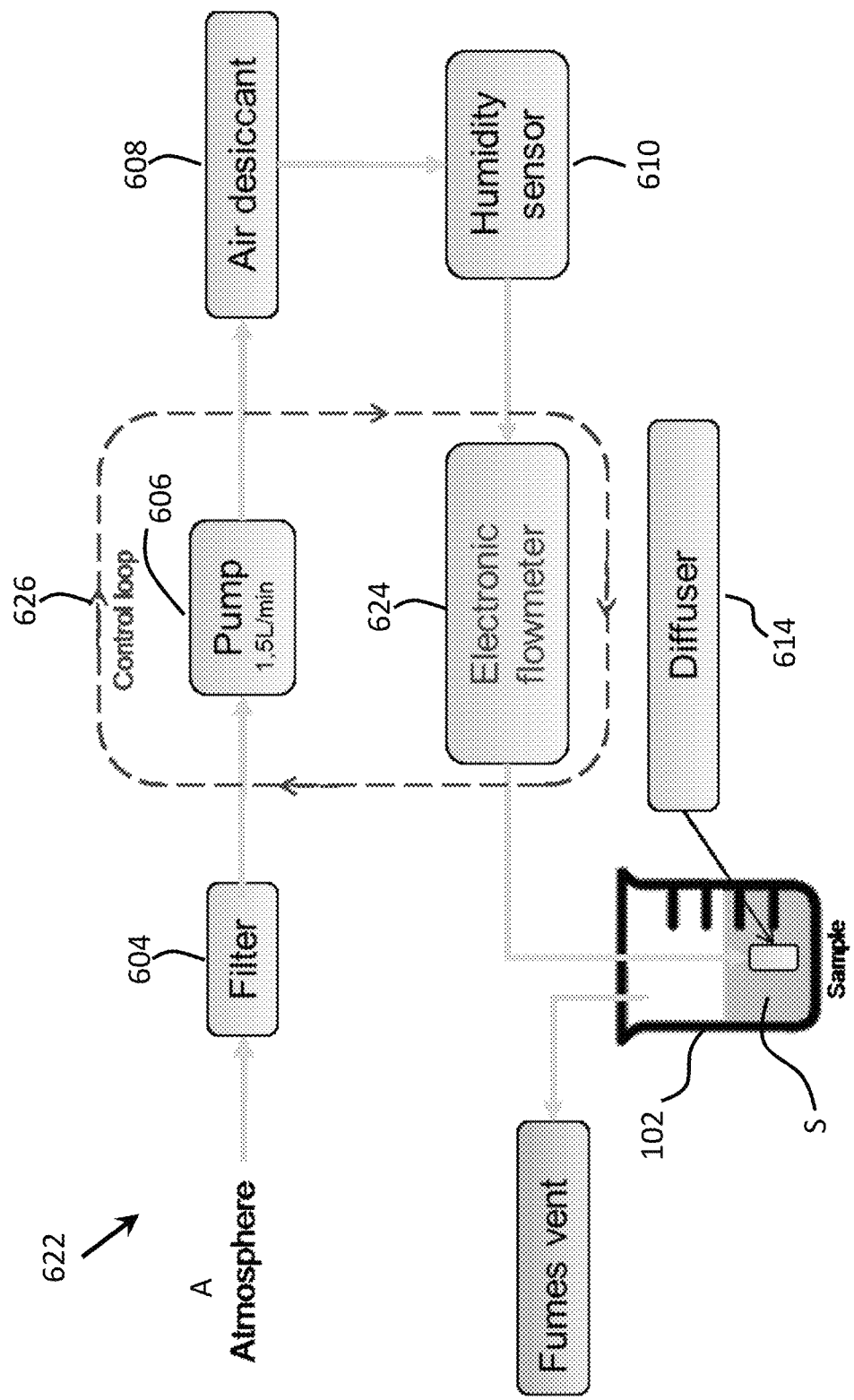
FIG. 6B is a diagram that illustrates an example operation of an automatic fuel sample aeration procedure.

FIG. 6B illustrates an alternate aeration sequence 622 for automatically controlling the airflow during the test method, according to one or more embodiments. As with the manual aeration sequence 602, the aeration sequence 622 similarly includes utilization of the filter 604, the pump 606, the air desiccant 608, the humidity sensor 610, and the diffuser 614 arranged within the sample container 102. However, the aeration sequence 622 is performed automatically so that no manual action or adjustment is required to maintain the desired flow rate, thereby ensuring that the flow rate prescribed by the test method is utilized/obtained throughout the aeration sequence 622. In the illustrated embodiment, the aeration sequence 622 thus utilizes an electronic flowmeter 624 (in lieu of the variable area flowmeter 610 of the manual aeration sequence 602), and the pump 606 includes a control loop or controller 626 associated with the electronic flowmeter 624 to maintain the desired flow rate as the air A is pumped through the air desiccant 608 and the humidity sensor 610 during at least a portion of the automatically controlled aeration sequence 622. In one embodiment, the controller 626 is a servo control utilizing pulse width modulation to coordinate the operation of the pump 606 and the electronic flowmeter 624 such that the fuel sample S is appropriately aerated as prescribed. In other embodiments, however, the automatic airflow control of the aeration sequence 622 may be differently arranged, for example, the pump 606 and the electronic flowmeter 624 may include a plurality of sensors and use logic to maintain the prescribed flow rate.

As detailed above, the pump system 506 moves the fuel sample S at a steady rate from the sample container 102, through the test section 110 and across the heater tube 114, and finally into the waste container 104. Indeed, the test method prescribes that the fuel sample S should flow at a rate of 3 mL/min with a pressure of 500 pounds per square inch ("PSI"). This low flow rate, coupled with the variability of the mechanical properties of the fuel sample S (i.e., viscosity, density, etc.), may hinder the ability to use conventional pump systems (i.e., membrane pumps, piston pumps, etc.) in a reliable manner and thus adversely impact the accuracy of the test method results. Moreover, the flow rate may impact the quality of the thermal oxidation deposit formed on the heater tube 114. For example, at a low flow rate period, followed by a sharp increase in flow rate along with a large temperature gradient may result in axisymmetric instabilities (i.e., Taylor type toroidal vortices) near the hot surface, and these "local vortices," while not making the overall flow through the heater tube 114 turbulent, may operate to remove thin layers of the thermal oxidation deposit from the heater tube 114 (as it forms thereon). Thus, the pump system 506 utilized should provide a smooth and steady rate of flow so as to not damage the resulting thermal oxidation deposit.

In the past, conventional pump systems 506 have comprised a single syringe, meaning that the whole fuel volume (i.e., the fuel sample S) necessary for the test was contained in the single syringe. This generation of instrument, however, had numerous issues related to the size of the syringe, as well as its handling and leaking. For example, where the single syringe is utilized having a volume that is less than the total volume of sample fuel S needed for the test method, a pause or gap in flow is inevitable at the time of the intermediate aspirations. Other prior pump systems 506 have utilized high-performance liquid chromatography ("HPLC") pumps with dual pistons. HPLC pumps, however, are not satisfactory because there are micro ruptures at the end of each piston cycle. In addition, HPLC pumps are expensive to purchase and maintain.

In one embodiment, the pump system 506 has a dual syringe arrangement that ensures steady flow of the fuel sample S, regardless of the mechanical properties of the fuel sample S. FIG. 7 illustrates a pump system 702 utilizing a dual syringe/piston arrangement, according to one or more embodiments. As illustrated, the pump system 702 includes two (2) syringes or piston assemblies 704,706 that are respectively operated by a pair of motors 708,710. Thus, the first motor 708 operates to drive the first syringe assembly 704, whereas the second motor 710 operates to drive the second syringe assembly 706.

In the illustrated embodiment, each syringe assembly 704,706 includes a barrel 712 that is hollow and defines an interior volume 714 into which the fuel sample S may be pumped. The barrel 712 includes a tip portion 716 at a first end of the barrel 712 and an open end 718 at a second end of the barrel 712 that is oriented opposite of the tip portion 716. Each syringe assembly 704,706 also includes a plunger (or piston) 720 that extends into the interior volume 714 of the barrel through the open end 718 thereof, and may slide therewithin so as to increase or decrease the amount of the fuel sample S that may fill the interior volume 714. The piston 720 includes a head portion 722 and a shaft 724 that is connected to a rear face of the head portion 722. The head portion 722 is dimensioned to fit within the interior volume 714 such that its outer perimeter or periphery abuts an interior wall of the barrel 712, thereby forming a seal between the periphery of the head portion 722 and the interior wall of the barrel 712 to inhibit the fuel sample S from leaking or flowing out of the open end 718 of the barrel 712. The shaft 724 extends away from the rear face of the head portion 722, through the interior volume 714 and exits the barrel 712 via the open end 718.

In addition, the shaft 724 includes an end 726 that is arranged opposite the head 722 and operatively coupled to one of the motors 708,710. In one embodiment, the motors 708,710 are step motors that each include a ball screw transmission 728, that in turn drive the piston 720. In that embodiment, the ball screw transmissions 728 are connected to the end 726 of the shaft 724 to drive the head 722 of the plunger relative to the barrel 712, thereby varying the size of the interior volume 714. The feed speed of the piston 720 is imposed by the motors 708,710 via the ball screw transmission 728.

Each syringe assembly 704,706 also includes a pair of check valves 730,732 to control the flow of the fuel sample S entering and exiting the interior volume 714 of the barrel 712. Here, the check valves 730,732 are arranged at each tip portion 716. The first check valve 730 is arranged on an input line 734 that fluidly interconnects the sample container 102 to the interior volume 714 of the barrel 712, and permits flow of the fuel sample S from the sample container 102 into the interior volume 714 of the barrel 712, but not in the reverse direction. Similarly, the check valve 732 is arranged on a fluid output line 736 that fluidly interconnects the interior volume 714 to other downstream systems such as those utilized in the pre-filtration step 508, and permits flow from the barrel 712 to such downstream equipment, but not in the reverse direction.

The syringe assemblies 704,706 operate with an alternate firing sequence. For example, when the first syringe assembly 704 is drawing the fuel sample S into its respective barrel 712 (i.e., the suction phase), the second syringe assembly 706 is expelling the fuel sample S from its respective barrel 712 (i.e., the expulsion phase). With this arrangement, one of the syringe assemblies 704,706 is always performing an expulsion phase, thereby ensuring that the fuel sample S is provided to the downstream equipment at a constant flow rate, as prescribed by the test method.

The fuel sample S is drawn into and expelled out of the barrels 712, via axial movement of the piston 720, in and out of the barrels 712. When the piston 720 is pulled from the first syringe assembly 704 in a first direction X1 at a constant speed, a volume of the fuel sample S is sucked from the sample container 102. At the same moment, the piston 720 of the second syringe assembly 706 is pushed into the barrel 712 at a fixed speed. When pushing the piston 720 into the second syringe assembly 706, the fuel sample S in the respective barrel 712 is expelled at a rate that is dependent on the diameter of the head portion 722 and the speed at which it is displaced within the interior volume 714. The pair of check valves 730,732 ensure the alternating operation of the suck phase and the expulsion phase as detailed above and, in some embodiments, the pair of check valves 730,732 are active valves, whereas in other embodiments the pair of check valves 730,732 are passive valves.

The pump system 702 pumps the fuel sample S with an imperceptible flow fluctuation during the switch from one of the syringe assemblies 704,706 to the other. This is achieved by accelerating one of the pistons 720 at the beginning of its stroke in the bottom of the barrel 712 (i.e., proximate to the open end 718), as it travels in the first direction X2 towards the tip 716 and simultaneously decelerating the second piston 720 when it nears the end of its stroke (i.e., proximate to the tip 716). Thus, the deceleration of one piston 720 (e.g., of the first syringe assembly 704) at the end of the cycle is compensated by the acceleration of the other piston 720 (e.g., of the second syringe assembly 706), and vice versa. This phasing is provided such that the sum of the piston 720 speeds of the first and second syringe assembly 704,706 is always equal to the nominal feed rate, thereby ensuring a constant rate of flow rate for the chosen diameter of the barrel 712. In the illustrated embodiment, the interior volume 714 of each barrel 712 is 5 mL, and the fuel sample S flow rate is 3 mL/min. In the illustrated embodiment, the switch period from one of the syringe assemblies 704,706 to the other is about 20% of the total cycle time, which thereby eliminates any flow fluctuation.

As the fuel sample S is pumped through the test section 110, a steady current is applied to the heater tube 114 via the bus bars 122a,122b and, depending upon the temperature and/or quality of the fuel sample utilized in a particular test, a thermal oxidation deposit may form on the heating tube 114 as a visible film. The heater tube 114 is maintained at a relatively high temperature, for example, at 260° C.; however, this temperature may be higher or lower in some applications. The current applied to the heater tube 114 is controlled to maintain a steady temperature at the point of measurement.

Figure 8:
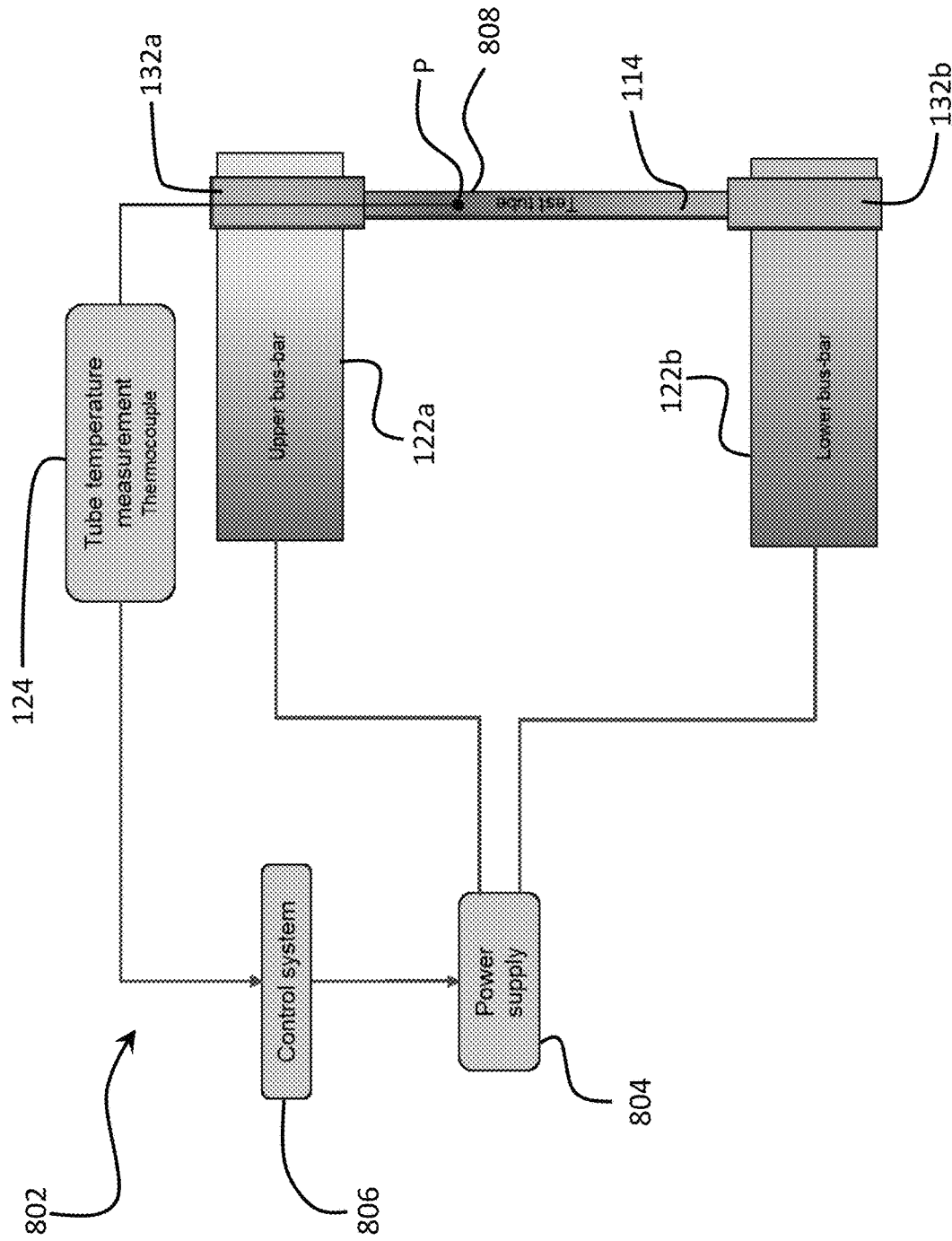
FIG. 8 is a diagram illustrating the operation of a heating system utilized in the rig of FIG. 1A.

FIG. 8 is a diagram that illustrates a conventional heating system 802 for heating the heater tube 114 via the bus bars 122a,122b. As illustrated, the conventional heating system 802 includes a power supply 804, a control system 806, a thermocouple 124 that measures a hot spot 808 of the heater tube 114 at a point P thereon, and the pair of bus bars 122a,122b that secure the heater tube 114. The heater tube 114 is resistively heated by the conductance of high amperage, low voltage current from the power supply 804 through the heater tube 114, which results in the heater tube 114 having a thermal profile as illustrated. Here, the position of the point P of measurement of the thermocouple 124 is located inside the heater tube 114, and is fixed by the length of the shoulder 132a,b of the heater tube 114, which per the test method is 39 mm. Therefore, this 39 mm point is in the hottest region (i.e., the hot spot 808) of the heater tube 114 utilized in the test method.

In the illustrated embodiment, the bus bars 122a,122b are relatively heavy and water-cooled so that they incur a relatively minimal temperature increase when supplied with current. The control system 806 serves as an indicator and/or controller. For example, it may automatically control the temperature and vary the power supplied from the power supply 804 as needed so that a steady source of heat is provided to the bus bars 122a,122b and heater tube 114. Accordingly, the heating system 802 may be utilized to maintain a target temperature, for example, 260° C., as prescribed by the test method. The control system 806 may alternatively provide for manual operation and thus provide a technician only a temperature readout so that he or she may manually adjust the temperature as needed.

The thermal profile of the heater tube 114 and, therefore, the position of the hot spot 808 thereon, may be influenced by numerous factors. These factors include the thermal properties of the fuel sample S, the temperature of the bus bars 122a,122b, and the temperature difference (ΔT) between the bus bars 122a,122b. In addition, the ability to control the thermal profile of the heater tube 114 may improve test method results and reproducibility of the same. Conventional instruments, however, do not include control systems that permit fine-tuning of the heater tube 114 thermal profile. For example, while existing instruments do include cooling systems that remove heat going into the bus bars 122a,122b by conduction from the hot heater tube 114, technicians may not control these existing cooling systems to optimize the heat profile of the heater tube 114.

Figure 9A:
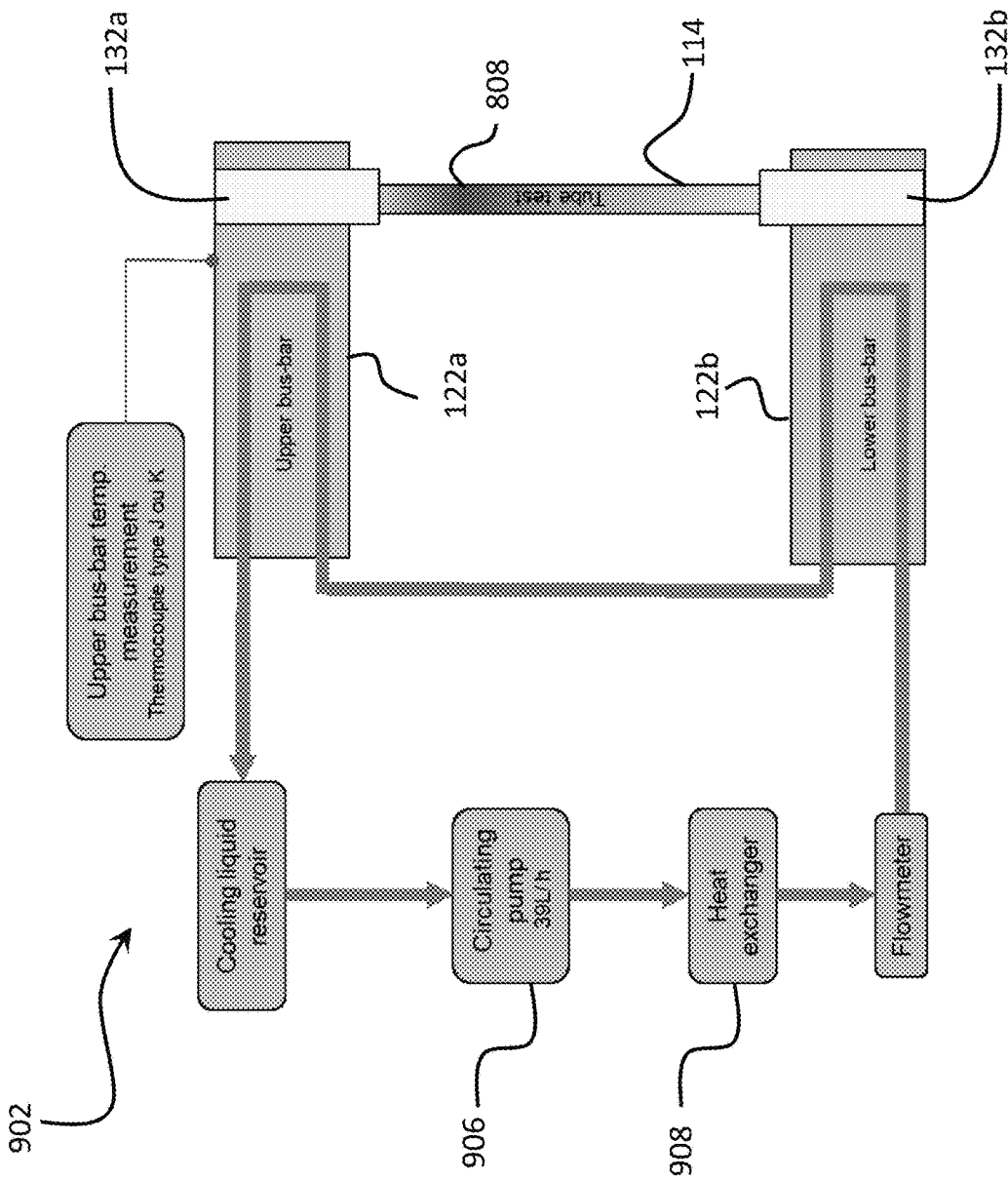
FIG. 9A is a diagram illustrating the operation of a bus bar cooling system utilized in the rig of FIG. 1A.
Figure 9B:
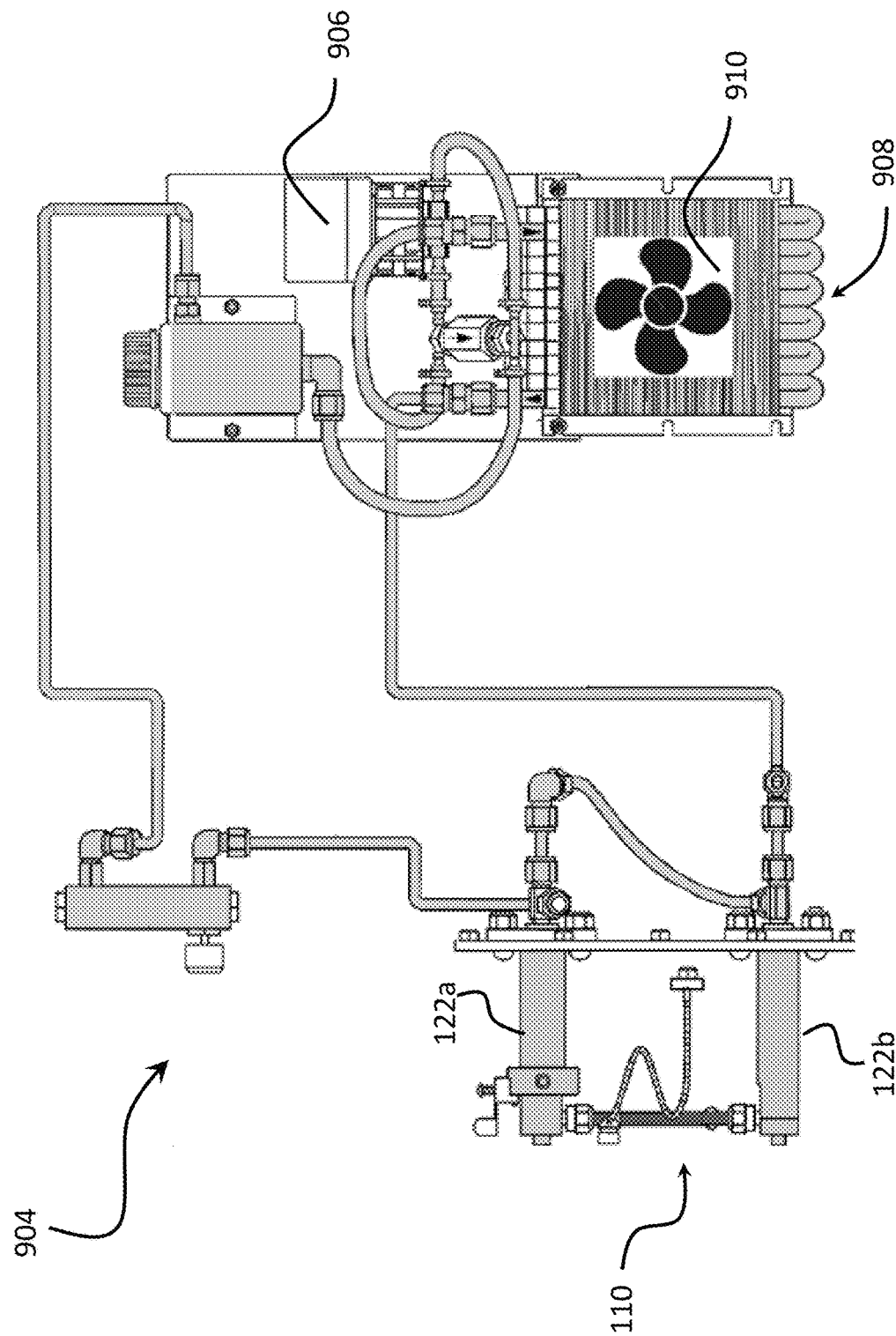
FIG. 9B is a schematic of the bus bar cooling system of FIG. 9A.

The bus bars 122a,122b of existing rigs 100 are cooled via water cooling systems that circulate water along a single path that flows through each bus bar 122a,122b. The water may be provided from an external source, for example a laboratory sink, or existing instruments may include an internally circulated and radiator cooled water system to circulate water. FIG. 9A is a diagram illustrating how an existing bus bar water cooling system 902 operates, and FIG. 9B illustrates an exemplary internal cooling system 904 that may be integrated into the existing instruments. These existing systems, however, are not temperature controlled, as they simply include a liquid pump 906 that circulates a liquid through the bus bars 122a,122b and then into a heat exchanger 908 that is associated with a fan 910 that blows air at ambient temperature, thereby cooling the liquid.

During operation of existing instruments, the initially unheated fuel sample S is introduced into the sleeve 112 proximate the lower bus bar 122b, is heated along the length of the heater tube 114 while flowing upward there-along, and exits the sleeve 112 proximate to the top bus bar 122a at a higher temperature. Fuel samples S comprising fuels with good heat transfer properties will, however, decrease the temperature of the lower bus bar 122b, but such fuel samples S will not impart the same effect to the upper bus bar 122a. This will in turn affect the heat profile of the heater tube 114, for example, by skewing the size of the hot spot 808 and/or by moving the hottest point P even closer to the upper shoulder 132a. These effects may adversely impact the test method results, as the temperature control system 806 is designed to take temperature measurements from a single point that is supposed to be the hottest point P on the heater tube 114; however, when the temperature profile is skewed and the hottest point P is shifted upwards along the heater tube 114, the temperature control system 806 will no longer be measuring the hottest point P, and will therefore provide inaccurate results. Moreover, when performing successive tests, for example, when several tests are performed in quick succession, the cooling fluid may become warmer and the thermal conditions of the heater tube 114 will not be identical for each of the subsequent tests.

Figure 10:
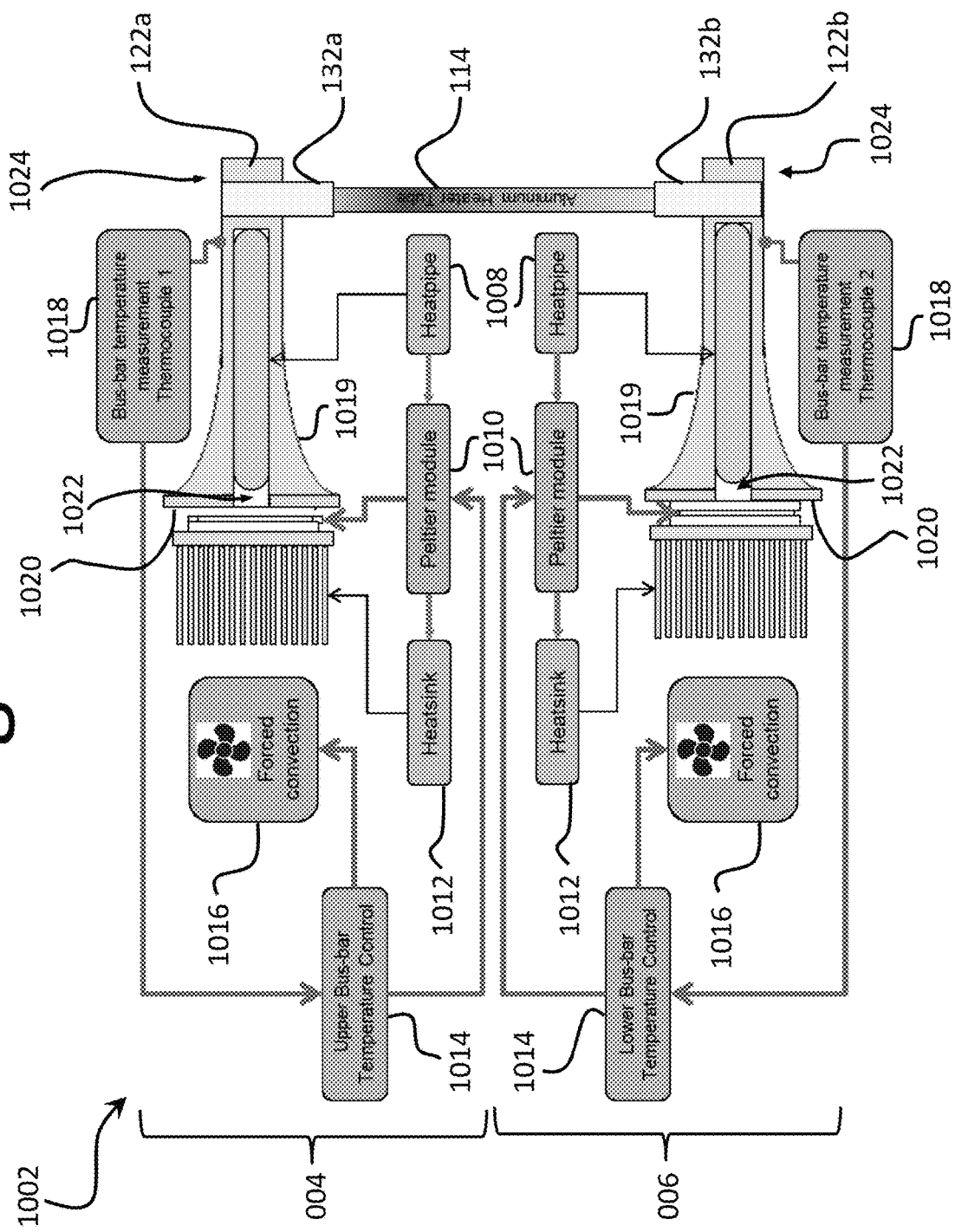
FIG. 10 is schematic illustrating an example operation of a bus bar cooling system that independently controls the separate bus bars.

FIG. 10 illustrates a temperature system 1002 for controlling temperature in the bus bars 122a,122b, according to one or more embodiments. The temperature system 1002 individually controls the temperature of each of the bus bars 122a,122b such that they are controlled independently of each other, thereby maintaining a constant thermal profile of the heater tube 114. In this way, the temperature difference ($\Delta T$) between the bus bars 122a,122b may be minimized and/or locked or set to a desired value. In addition, by locking the temperature difference ($\Delta T$) between the top and bottom bus bars 122a,122b, the temperature system 1002 may also limit the effects of the variability of the thermal properties of the tested fuel samples S.

The temperature system 1002 maintains a constant thermal profile of the heater tube 114 as a function of the test method temperature (e.g., 260° C. according to the test method). To do this, the temperature of each bus bar 122a,122b is perfectly controlled, and their temperature profiles are based on a typical temperature profile extracted from existing instruments in order to guarantee perfectly correlated results. The reproduced profile is the image of tests performed under normal ambient temperature and non-successive testing conditions. Moreover, if the test method protocols change or evolve in the future to require, for example, that the upper and lower bus bars 122a,122b maintain the same temperature (e.g., 35° C.), the temperature system 1002 will be compatible with such a new requirement while the existing instruments utilizing liquid circulation will be unable to satisfy such new requirement.

As illustrated, the temperature system 1002 includes an upper bus bar sub-system 1004 and a lower bus bar sub-system 1006 that control the temperature in the upper and lower bus bars 122a,122b, respectively. Each of the bus bar sub-systems 1004,1006 includes a cooling module 1010, a heat sink 1012, a controller 1014, a forced convection device 1016, and a thermocouple 1018 that measures the temperature of its respective bus bar 122a,122b. In the illustrated embodiment, the cooling module 1010 is a Peltier element and the forced convection device 1016 is a fan, but other cooling modules 1010 and/or forced convection devices 1016 may be utilized without departing from the present disclosure. As will be appreciated, each of the bus bar sub-systems 1004,1006 include a separate controller 1014 and componentry so that they may individually adjust the heat extracted from the bus bars 122a,122b by a respective heat pipe 1008.

Electric power is supplied to the cooling module 1010 and, therefore, the amount of thermal energy transferred from the bus bars 122a,122b to their respective heat sink 1012 is controlled by a temperature measurement carried out on each of the bus bars 122a,122b. The measuring point utilized for these temperature measurements is located on the bus bars 122a,122b at a point that is close to the interface with the heater tube 114 and may each, for example, be located at the same point of measurement as made on bus bars of existing instruments.

The bus bars 122a,122b may have geometries that optimize heat transfer. For example, an exterior profile or shape 1019 of the bus bars 122a,122b may be contoured as illustrated so as to be able to use the entire exchange surface of the cooling module 1010. Also in the illustrated embodiment, each bus bar 122a,122b includes a base 1020 and a bore 1022 extending inward therefrom, towards a tapered end 1024 that holds or secures the heater tube 114; and the heat pipes 1008 are inserted into the bores 1022 of the bus bars 122a,122b. Since the thermal conductivity of the heat pipe 1008 is higher than that of the bus bars 122a,122b (e.g., which may be made from brass), calories are more efficiently transferred from one end of each bus bar 122a,122b to the other. The temperature difference ($\Delta T$) between their measuring points (i.e., the measuring points of the thermocouples 1018) and the bearing surface of the cold face of the cooling module 1010 may be reduced, which improves the efficiency of the cooling system 1002 and the response time of the control loop. Thus, the temperature system 1002 provides independent thermal control of the separate bus bars 122a,122b, while eliminating the impact of ambient temperature compared to a cooling solution based solely on heat exchange with the ambient temperature.

FIG. 11A illustrates a clamping system 1102 that is utilized to secure the lower shoulder 132b of the heater tube 114 (within the sleeve 112) to the lower bus bar 122b. As illustrated, the clamping system 1102 includes a plate 1104 that is moveably positioned proximate to an end face 1106 of the lower bus bar 122b, and arranged to compress or clamp the lower shoulder 132b of the heater tube 114 that is positioned within the lower bus bar 122b. The clamping system 1102 further includes a pair of screws 1108 that extend through an outer surface 1110 and interior surface (obscured from view) of the plate 1106 and into the end face 1106 of the lower bus bar 122*b*. As will be appreciated, a technician may tighten or loosen the screws 1108 to compress or depress the plate 1104 relative to the lower bus bar 122*b*. Thus, when the lower shoulder 132*b* of the heater tube 114 (that is secured within the sleeve 112) is positioned between the interior face (obscured from view) of the plate 1104 and the end face 1106 of the lower bus bar 122*b*, the technician may tighten or loosen the screws 1108 to secure or remove the test section 110. In some embodiments, either or both of the interior face (obscured from view) of the plate 1104 and the end face 1106 of the lower bus bar 122*b* are contoured to receive the lower shoulder 132*b* of the heater tube 114. In addition, the screws 1108 may include a lever 1112 extending therefrom to facilitate tightening and loosening of the same. It will be appreciated that, while note illustrated, the clamping system 1102 is similarly arranged at the upper bus bar 122*a* to secure/unsecure the upper shoulder 132*a* thereto.

To install or uninstall the sleeve 112 and heater tube 114 assembly (i.e., the test section 110) relative to the lower bus bar 122*b*, the technician must move the plate 1104 so that the plate 1104 no longer obstructs the location on the end face 1106 that receives the lower shoulder 132*b* of the heater tube 114. In one method, the technician must fully remove one (1) of the screws 1108 and then loosen the other one (1) of the screws 1108 such that the plate 1104 may pivot on the (remaining) screw 1108, thereby un-obstructing and presenting the lower shoulder 132*b* within the end face 1106 of the lower bus bar 122*b*. Alternatively, the technician may remove both of the screws 1108 to fully remove the plate 1104 from the end face 1106 of the lower bus bar 122*b* to install or uninstall the test section 110. While not described, it will be appreciated that the foregoing described operation of the clamping system 1102 may be similarly utilized at the upper bus bar 122*a* to secure/unsecure the upper shoulder 132*a* thereto.

Alternate clamping systems may be utilized, however, that do not necessitate two (2) screws and that provide improved electrical and/or thermal contact between the shoulders 132*a*,132*b* and the bus bars 122*a*,122*b*. For example, FIG. 11B illustrates a clamping system 1120, according to one or more embodiments. As detailed below, the illustrated clamping system 1120 utilizes a single screw that may be removed to install or uninstall the heater tube 114, and may provide enhanced thermal and electrical contact. While the clamping system 1120 of FIG. 11B may be utilized with either or both of the upper and lower bus bars 122*a*,122*b*, it is hereinafter described with use on a single unspecified bus bar 122 that could be utilized as either the upper or lower bus bar 122*a*,122*b*.

As illustrated, the bus bar 122 utilized in the clamping system 1120 is forked at the tapered end 1024. Thus, the tapered end 1024 of the bus bar 122 includes a pair of forks or prongs 1122*a*,1122*b* extending therefrom away from the base 1020 of the bus bar 122. The pair of prongs 1122*a*, 1122*b* define a recess or gap 1124 there-between. Here, gap 1124 is sized such that the shoulder 132*a*,132*b* of the heater tube 114 may be inserted or retracted there trough as hereinafter described. In addition, the tapered end 1024 may be hollow to define a threaded bore 1126 that extends into the bus bar 122 for at least the length of prongs 1122*a*,1122*b*.

In the illustrated embodiment, the clamping system 1120 further includes a screw 1128 having a threaded portion 1130 that is received within and meshes with the threaded bore 1126 of the bus bar 122. Also, the clamping system 1120 includes a plate 1132 that is positioned within the gap 1124 between the pair of prongs 1122*a*,1122*b*, and the plate 1132 is arranged to slide between the prongs 1122*a*,1122*b* towards and away from an interior face 1134 of the bus bar 122 that will abut one of the shoulders 132*a*,132*b* of the heater tube 114. In operation, one of the shoulders 132*a*, 132*b* will be disposed proximate to the interior face 1134 of the bus bar 122, and the screw 1128 may then be rotated to drive the threaded portion 1130 thereof into or out of the threaded bore 1126, which in turn drives the plate 1132 towards or away from the interior face 1134 and thus compresses or de-compresses one of the shoulders 132*a*, 132*b* that is positioned there-between. When the screw 1128 and the plate 1132 are withdrawn from the tapered end 1024 of the bus bar 122, the gap will be unobstructed such that the shoulder 132*a*,132*b* of the heater tube 114 may be inserted or withdrawn. In the illustrated embodiment, the plate 1132 and the interior face 1134 each include a seat 1132',1134' that is contoured to receive the shoulders 1132*a*,1132*b'*.

Also in the illustrated embodiment, the screw 1128 is hollow and includes a bore 1136 having a narrow portion 1137*a* and a wide portion 1137*b*, and the plate 1132 includes a shaft 1138 that is hollow and defines a bore 1140 that is coaxial with the bore 1136 of the screw 1128. As illustrated, the shaft 1138 and its bore 1140 extend from the plate 1132, through the narrow portion 1137*a* and into the wide portion 1137*b* of the bore 1136 of the screw 1128 in a direction away from the base 1020 of the bus bar 122.

A locking device 1142 may be be utilized to limit or inhibit the amount of axial movement of the plate 1132 within the gap 1124 relative to the screw 1128 while permitting rotation of the screw 1128 relative to the plate 1132. The locking device 1142 is secured within the bore 1140 of the plate 1132. In addition, the locking device 1142 may include a flange 1144 that floats within the wide portion 1137*b* of the bore 1136 of the screw 1128, and abuts a shoulder 1146 within the bore 1136 of the screw 1128 (i.e., that is disposed between the narrow and wide portions 1137*a*,1137*b*) when the screw 1128 is retracted from the bore 1126 of the bus bar 122. Also, the plate 1132 may be attached to the screw 1128 to permit relative rotation between the plate 1132 and the screw 1128, but to inhibit the shaft 1138 of the plate 1132 from being fully withdrawn from the bore 1136 of the screw 1128 via interaction between the flange 1144 and the shoulder 1146. Thus, when the screw 1128 is withdrawn from the threaded bore 1126 of the bus bar 122, the plate 1132 (that is attached to the locking device 1142) will be pulled by the (rotating) screw 1128 in the axial direction away from the base 1020 of the bus bar 122. Stated differently, rotation of the screw 1128 translates to an axial displacement of the plate 1132 within the gap 1124. Accordingly, the plate 1132 is carried by (or retracted with) the screw 1128, which may be removed from the tapered end 1024 of the bus bar 124 to expose the gap 1124 so that the shoulder 132*a*,132*b* of the heater tube may be assembled or disassembled relative thereto, which facilitates removal of the heater tube 114 from the bus bar 122.

In some embodiments, the bus bars 122 may one or both of a pair of recesses 1018*a*,1018 that are disposed at an upper or lower sides of the bus bar 122 and arranged to receive one of the thermocouple 1018 of the temperature system 1002, as detailed above.

Therefore, the disclosed systems and methods are well-adapted to attain the ends and advantages mentioned, as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

The use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A pump system for moving a fuel sample through a thermal oxidation rig, the pump system comprising:
   a first and second syringe assembly, each syringe assembly having a hollow barrel that defines a volume for holding the fuel sample, a tip disposed at an upper end of the barrel, an open end disposed at a lower end of the barrel, each syringe assembly having an inlet valve and an outlet valve;
   a pair of pistons that are each arranged to slide within one of the barrel volumes, each piston having shaft that extends into the volume through the open end of the barrel and connects to a head portion that abuts an interior wall of the hollow barrel so that the volume is sealed from the open end of the barrel, and
   a pair of motors, each of the motors is coupled to one of the pistons and independently controlled so that a flow rate of the fuel sample remains constant, wherein each of the motors controls a stroke of its respective piston such that the pistons accelerate and decelerate simultaneously.

2. The pump system of claim 1, wherein the pump system further comprises a common inlet line that feeds both the inlet valve of the first syringe assembly and the inlet valve of the second syringe assembly.

3. The pump system of claim 2, wherein the common inlet line is connected to a sample container that holds the fuel sample.

4. The pump system of claim 1, wherein the pump system further comprises a common outlet line that receives from both the outlet valve of the first syringe assembly and the outlet valve of the second syringe assembly.

5. The pump system of claim 4, wherein the fuel sample is moved through the common outlet line at a constant flow.

6. The pump system of claim 1, wherein the pump system further comprises a pair of ball screw transmissions, each ball screw transmission interposed between the respective motor and piston.

7. The pump system of claim 1, wherein the pistons accelerate and decelerate simultaneously, with the piston of the second syringe assembly when located proximate the lower end of the barrel being accelerated by the motor associated therewith toward the upper end of the barrel at a beginning of the stroke, while simultaneously decelerating the piston of the first syringe assembly via the motor associated therewith when nearing the upper end of the barrel at an end of the stroke.

8. The pump system of claim 1, wherein each of the motors controls the stroke of its respective piston such that the pistons accelerate and decelerate simultaneously, wherein, at a beginning of the stroke when the piston is located proximate the lower end of the barrel, the motor associated with the first syringe assembly accelerates the piston coupled thereto towards the upper end of the barrel, and, at an end of the stroke when the piston is proximate the upper end of the barrel, the motor associated with the second syringe assembly decelerates the piston coupled thereto.

9. The pump system of claim 1, wherein the motor of each of the syringe assemblies drives the respective piston at a same speed during both a suction phase and an expulsion phase.

* * * * *